United States Patent
Meki et al.

(10) Patent No.: US 11,420,040 B2
(45) Date of Patent: Aug. 23, 2022

(54) METHODS, SYSTEM, AND COMPUTER READABLE MEDIA FOR A ROTATIONAL SPEED-BASED CONTROL SYSTEM FOR VENTRICULAR ASSIST DEVICES

(71) Applicant: University of Louisville Research Foundation, Inc., Louisville, KY (US)

(72) Inventors: Moustafa Hassan Meki, Prospect, KY (US); Guruprasad Anapathur Giridharan, Louisville, KY (US); Palaniappan Sethu, Mountain Brook, AL (US); Ayman Sabry El-Baz, Louisville, KY (US); Yu Wang, Dalian (CN)

(73) Assignee: University of Louisville Research Foundation, Inc., Louisville, KY (US)

( * ) Notice: Subject to any disclaimer, the term of this patent is extended or adjusted under 35 U.S.C. 154(b) by 84 days.

(21) Appl. No.: 16/678,897

(22) Filed: Nov. 8, 2019

(65) Prior Publication Data
US 2020/0147284 A1   May 14, 2020

Related U.S. Application Data

(60) Provisional application No. 62/757,377, filed on Nov. 8, 2018.

(51) Int. Cl.
*A61M 60/10* (2021.01)
*A61M 60/432* (2021.01)
(Continued)

(52) U.S. Cl.
CPC .......... *A61M 60/50* (2021.01); *A61M 60/148* (2021.01); *A61M 2205/3327* (2013.01);
(Continued)

(58) Field of Classification Search
CPC .............. A61M 60/205; A61M 60/148; A61M 2205/3365; A61M 2210/125;
(Continued)

(56) References Cited

U.S. PATENT DOCUMENTS

2003/0045772 A1* 3/2003 Reich .................... A61M 60/50
600/18

OTHER PUBLICATIONS

AlOmari et al., "Non-invasive estimation of pulsatile flow and differential pressure in an implantable rotary blood pump for heart failure patients," Physiol Meas, vol. 30, pp. 371-386, Apr. 2009.
(Continued)

*Primary Examiner* — Jon Eric C Morales
(74) *Attorney, Agent, or Firm* — Jenkins, Wilson, Taylor & Hunt, P.A.

(57) ABSTRACT

Methods, systems, and computer readable media for controlling ventricular assist devices are disclosed. In some embodiments, the method includes receiving at least one reference pump speed differential associated with a pump of a ventricular assist device; determining a filtered pump speed differential associated with the pump of a ventricular assist device; and adjusting, using a feedback based controller algorithm, current to the pump based on the at least one reference pump speed differential and the filtered pump speed differential. In some embodiments, the system includes a controller implemented using the non-transitory computer readable medium, wherein the controller is configured for receiving at least one reference pump speed differential associated with a pump of a ventricular assist device; determining a filtered pump speed differential associated with the pump of a ventricular assist device; and adjusting current to the pump based on the at least one reference pump speed differential and the filtered pump speed differential.

16 Claims, 12 Drawing Sheets

(51) Int. Cl.
  *A61M 60/50* (2021.01)
  *A61M 60/148* (2021.01)
(52) U.S. Cl.
  CPC ............... *A61M 2205/3365* (2013.01); *A61M 2210/125* (2013.01)
(58) Field of Classification Search
  CPC .......... A61M 2205/04; A61M 2205/33; A61M 60/268; A61M 60/562; A61M 2205/3334; A61M 60/05
  See application file for complete search history.

(56) References Cited

OTHER PUBLICATIONS

AlOmari et al., "Developments in control systems for rotary left ventricular assist devices for heart failure patients: a review," Physiol Meas, vol. 34, pp. R1-27 (2013).
Amacher et al., "Control of ventricular unloading using an electrocardiogram-synchronized Thoratec paracorporeal ventricular assist device," J Thorac Cardiov Surg. vol. 146, No. 3, pp. 710-717 (2013).
Ambardekar et al., "Changes in aortic wall structure, composition, and stiffness with continuous-flow left ventricular assist devices: a pilot study," Circ Heart Fail, vol. 8, pp. 944-952 (2015).
Ambardekar et al., "Coronary Artery Remodeling and Fibrosis With Continuous-Flow Left Ventricular Assist Device Support," Circ Heart Fail, vol. 11, No. 5, e004491 pp. 1-12 (2018).
Ayre et al., "Non-invasive flow estimation in an implantable rotary blood pump: a study considering non-pulsatile and pulsatile flows," Physiol Meas, vol. 24, pp. 179-189, Feb. 2003.
Ayre et al., "Sensorless Flow and Head Estimation in the VentrAssist Rotary BloodPump," Artificial Organs, vol. 24, pp. 585-588, 2000.
Bozkurt et al., "Arterial pulsatility improvement in a feedback-controlled continuous flow left ventricular assist device: an ex-vivo experimental study," Med Eng. Phys. vol. 36, No. 10, pp. 1288-1295 (2014).
Brancato et al., "An Implantable Intravascular Pressure Sensor for a Ventricular Assist Device," Micromachines, vol. 7, p. 135 (2016).
Bullister et al., "Physiologic Control Algorithms for Rotary Blood Pumps Using Pressure Sensor Input," Artificial Organs, vol. 26, pp. 931-938 (2002).
Chen et al. "Physiological Control of Left Ventricular Assist Devices Based on Gradient of Flow," Proceedings of the 2005, American Control Conference, 2005, Portland, OR, USA, 2005, pp. 3829-3834 vol. 6.
Cheng et al., "Comparison of continuous-flow and pulsatile-flow left ventricular assist devices: is there an advantage to pulsatility?," Annals of Cardiothoracic Surgery, vol. 3, pp. 573-581, Jun. 27/accepted 2014.
Choi et al., "Hemodynamic controller for left ventricular assist device based on pulsatility ratio," Artif Organs, vol. 31, No. 2, pp. 114-125 (2007).
Couperus et al., "Pump Speed Optimization in Stable Patients with a Left Ventricular Assist Device," ASAIO Journal, vol. 63, pp. 266-272, (2017).
Cox et al., "A mathematical model to evaluate control strategies for mechanical circulatory support," Artif Organs, vol. 33, No. 8, pp. 593-603 (2009).
Farrar et al., "Design Features, Developmental Status, and Experimental Results With the Heartmate III Centrifugal Left Ventricular Assist System With a Magnetically Levitated Rotor," ASAIO Journal, vol. 53, pp. 310-315, 2007.
Frazier, "Unforeseen consequences of therapy with continuous-flow pumps," Circ Heart Fail vol. 3, pp. 647-649 (2010).
Frazier et al., "Optimization of axial-pump pressure sensitivity for a continuous-flow total artificial heart," J Heart Lung Transplant, vol. 29, pp. 687-691, Jun. 2010.
Fukamachi et al., "An innovative, sensorless, pulsatile, continuous-flow total artificial heart: device design and initial in vitro study," J Heart Lung Transplant, vol. 29, No. 1, pp. 13-20 (2010).
Fukamachi et al., "Preload Sensitivity in Cardiac Assist Devices," The Annals of Thoracic Surgery, vol. 95, pp. 373-380 (2013).
Gaddum et al., "Starling-Like Flow Control of a Left Ventricular Assist Device: In Vitro Validation," Artificial Organs, vol. 38, pp. E46-E56, 2014.
Gao et al., "A pulsatile control algorithm for continuous-flow pump for heart recovery," ASAIO J vol. 58, No. 4, pp. 343-352 (2012).
Garcia et al., "Effects of pulsatile- and continuous-flow left ventricular assist devices on left ventricular unloading," J Heart Lung Transpl vol. 27, pp. 261-267 (2008).
Giridharan & Mikhail, "Physiological Control of Blood Pumps Using Intrinsic Pump Parameters: A Computer Simulation Study," Artificial Organs, vol. 30, pp. 301-307, 2006.
Giridharan et al., "Modeling and control of a brushless DC axial flow ventricular assist device," ASAIO J, vol. 48, pp. 272-289, May-Jun. 2002.
Giridharan et al., "Predicted hemodynamic benefits of couterpulsation therapy using a superficial surgical approach," ASAIO J vol. 52, No. 1, pp. 39-46 (2006).
Guan et al., "Physiologic benefits of pulsatile perfusion during mechanical circulatory support for the treatment of acute and chronic heart failure in adults," Artif Organs vol. 34, pp. 529-536 (2010).
Huang et al., "Pulse-pressure-enhancing controller for better physiologic perfusion of rotary blood pumps based on speed modulation," ASAIO J vol. 60, No. pp. 3269-3279 (2014).
Ising et al., "Flow modulation algorithms for continuous flow left ventricular assist devices to increase vascular pulsatility: a computer simulation study," Cardiovasc Eng Technol vol. 2, No. 2, pp. 90-100 (2011).
Ising et al., "Feasibility of pump speed modulation for restoring vascular pulsatility with rotary blood pumps," ASAIO J vol. 61, No. 5, pp. 526-532 (2015).
Jahren et al., "Analysis of pressure head-flow loops of pulsatile rotodynamic blood pumps," Artif Organs, vol. 38, No. 4, pp. 316-326 (2014).
Karantonis et al., "Noninvasive Pulsatile Flow Estimation for an Implantable Rotary Blood Pump," in 2007 29th Annual International Conference of the IEEE Engineering in Medicine and Biology Society, pp. 1018-1021 (Aug. 2007).
Konishi et al., "Dynamic systemic vascular resistance in a sheep supported with a Nimbus AxiPump," ASAIO J vol. 40, pp. M299-M302 (1994).
Lim et al., "Noninvasive average flow and differential pressure estimation for an implantable rotary blood pump using dimensional analysis," IEEE Trans Biomed Eng, vol. 55, pp. 2094-2101, Aug. 2008.
Malagutti et al., "Noninvasive average flow estimation for an implantable rotary blood pump: a new algorithm incorporating the role of blood viscosity," Artif Organs, vol. 31, pp. 45-52, Jan. 2007.
Mansouri et al., "Preload-based starling-like control for rotary blood pumps: numerical comparison with pulsatility control and constant speed operation," PLoS One vol. 10, p. e0121413 (2015).
Meki et al., "A Sensorless Rotational Speed-based Control System for Continuous Flow Left Ventricular Assist Devices," IEEE Transactions on Biomedical Engineering pp. 1-12 (2019).
Moscato et al., "Left Ventricle Afterload Impedance Control by an Axial Flow Ventricular Assist Device: A Potential Tool for Ventricular Recovery," Artificial Organs vol. 34, pp. 736-744 (2010).
Ochsner et al., "A physiological controller for turbodynamic ventricular assist devices based on a measurement of the left ventricular volume," Artif Organs. vol. 38, pp. 527-538 (2014).
Patel et al., "Dynamic change in aortic vascular stiffness in patients bridged to transplant with continuous-flow left ventricular assist devices," JACC: Heart Failure, vol. 5, pp. 449-459 (2017).
Patibandla et al., "Evaluation of the effect of diminished pulsatility as seen in continuous flow ventricular assist devices on arterial endothelial cell phenotype and function," J Heart Lung Transplant, vol. 35, pp. 930-932 (2016).

(56) References Cited

OTHER PUBLICATIONS

Pauls et al., "Evaluation of Physiological Control Systems for Rotary Left Ventricular Assist Devices: An In-Vitro Study," Ann Biomed Eng vol. 44, pp. 2377-2387 (2016).
Pennings et al., "Pump flow estimation from pressure head and power uptake for the HeartAssist5, HeartMate II, and HeartWare VADs," ASAIO J, vol. 59, pp. 420-426, Jul.-Aug. 2013.
Petrou et al., "Comparison of Flow Estimators for Rotary Blood Pumps: An In Vitro and In Vivo Study," Annals of Biomedical Engineering vol. 46, pp. 2123-2134 (2018).
Petrou et al., "Viscosity Prediction in a Physiologically Controlled Ventricular Assist Device," IEEE Transactions on Biomedical Engineering, pp. 1-1, 2018.
Pillay & Krishnan, "Modeling, simulation, and analysis of permanent-magnet motor drives. II. The brushless DC motor drive," IEEE Transactions on Industry Applications, vol. 25, pp. 274-279, 1989.
Salamonsen et al., "Theoretical Foundations of a Starling-Like Controller for Rotary Blood Pumps," Artificial Organs. vol. 36, pp. 787-796 (2012).
Saxton, Jr. & Andrews, "An ideal heart pump with hydrodynamic characteristics analogous to the mammalian heart," Trans Am Soc Artif Intern Organs, vol. 6, pp. 288-291, Apr. 10-11, 1960.
Segura et al., "Morphologic changes in the aortic wall media after support with a continuous-flow left ventricular assist device," J Heart Lung Transplant vol. 32, pp. 1096-1100 (2013).
Shi et al., Development of an Auto Calibration Method for the Implantable Blood Pressure Sensor in the Undulation pump ventricular assist device (UPVAD). 7th Asian-Pacific Conference on Medical and Biological Engineering, Berlin, Heidelberg pp. 66-69 (2008).
Simaan et al., A dynamical state space representation and performance analysis of a feedback-controlled rotary left ventricular assist device, IEEE Trans Control Syst Technol, vol. 17, No. 1 pp. 15-28 (2009).
Slaughter et al., "Advanced heart failure treated with continuous-flow left ventricular assist devices," N Engl J Med, vol. 361, pp. 2241-2251 (2009).
Slaughter et al., "Intraoperative evaluation of the HeartMate II flow estimator," J Heart Lung Transplant, vol. 28, pp. 39-43, Jan. 2009.
Soucy et al., "Fault detection in rotary blood pumps using motor speed response," ASAIO J, vol. 59, pp. 410-419, Jul.-Aug. 2013.
Soucy et al., "Defining pulsatility during continuous-flow ventricular assist device support," J Heart Lung Transplant vol. 32, pp. 581-587 (2013).
Soucy et al., "Rotary pump speed modulation for generating pulsatile flow and phasic left ventricular volume unloading in a bovine model of chronic ischemic heart failure," J Heart Lung Transplant vol. 34, No. 1, pp. 122-131 (2015).
Soucy et al., "Continuous-flow left ventricular assist device support improves myocardial supply: demand in chronic heart failure," Ann Biomed Eng vol. 45, pp. 1475-1486 (2017).
Stanfield et al., "In vitro pulsatility analysis of axial-flow and centrifugal-flow left ventricular assist devices," J Biomech Eng vol. 135:034505-1-034505-6 (2013).
Stevens et al., "Frank-starling control of a left ventricular assist device," Conf Proc IEEE Eng Med Biol Soc, vol. 2011, pp. 1335-1338, 2011.
Undar, "Benefits of pulsatile flow during and after cardiopulmonary bypass procedures," Artif Organs vol. 29, pp. 688-690 (2005).
Uriel et al., "Development of a Novel Echocardiography Ramp Test for Speed Optimization and Diagnosis of Device Thrombosis in Continuous-Flow Left Ventricular Assist Devices: The Columbia Ramp Study," Journal of the American College of Cardiology, vol. 60, pp. 1764-1775, Oct. 30, 2012/ 2012.
Uriel et al., "Long Term Outcomes for LVAD Patients Who Underwent Speed Optimization Using Pre-Discharge Ramp Test," The Journal of Heart and Lung Transplantation, vol. 32, p. S182, Apr. 1, 2013/ 2013.
Vandenberghe et al., "Hemodynamic modes of ventricular assist with a rotary blood pump: continuous, pulsatile, and failure," ASAIO J vol. 51, No. 6, pp. 711-718 (2005).
Voigt et al., "Suction detection for the MicroMed DeBakey Left Ventricular Assist Device," ASAIO J, vol. 51, pp. 321-328, Jul.-Aug. 2005.
Vollkron et al., "Development of a suction detection system for axial blood pumps," Artif Organs, vol. 28, pp. 709-716, Aug. 2004.
Wang & Simaan, "A Suction Detection System for Rotary Blood Pumps Based on the Lagrangian Support Vector Machine Algorithm," IEEE Journal of Biomedical and Health Informatics, vol. 17, pp. 654-663, 2013.
Wang et al., "Rotary blood pump control strategy for preventing left ventricular suction," ASAIO J, vol. 61, pp. 21-30, Jan.-Feb. 2015.
Wang et al., "Sensor-Based Physiologic Control Strategy for Biventricular Support with Rotary Blood Pumps," ASAIO J, vol. 64, pp. 338-350, May/Jun. 2018.
Wang et al., "Sensorless Physiologic Control, Suction Prevention, and Flow Balancing Algorithm for Rotary Biventricular Assist Devices," IEEE Transactions on Control Systems Technology, pp. 1-13, 2018.
Wang et al., "Suction prevention and physiologic control of continuous flow left ventricular assist devices using intrinsic pump parameters," ASAIO J, vol. 61, pp. 170-177, Mar.-Apr. 2015.
Wu et al., "An Advanced Physiological Controller Design for a Left Ventricular Assist Device to Prevent Left Ventricular Collapse," Artificial Organs vol. 27, pp. 926-930 (2003).

* cited by examiner

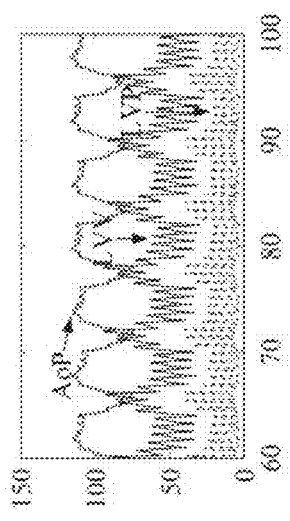
FIG. 3A
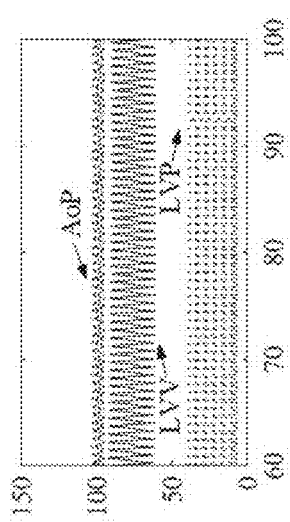
FIG. 3E
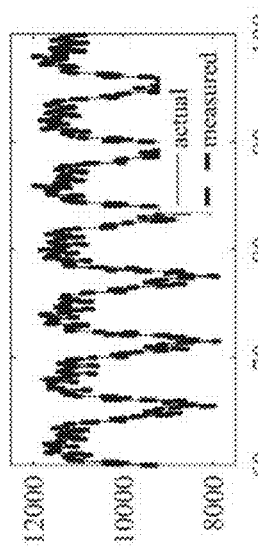
FIG. 3I
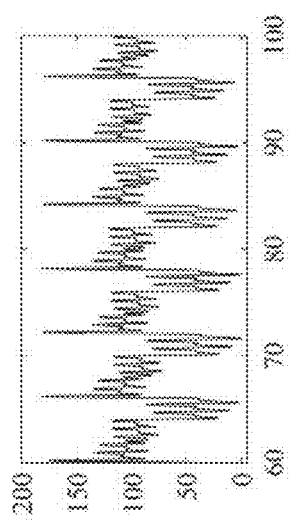
FIG. 3B
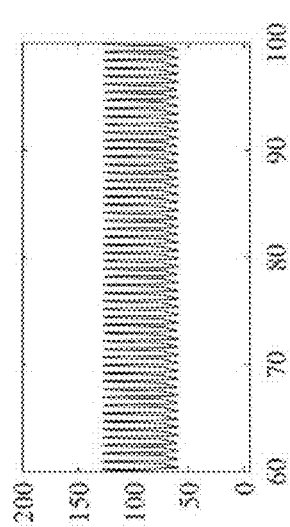
FIG. 3F
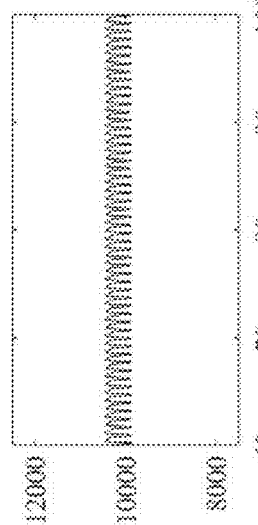
FIG. 3J
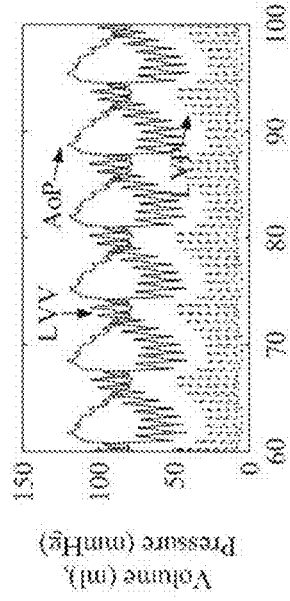
FIG. 3C
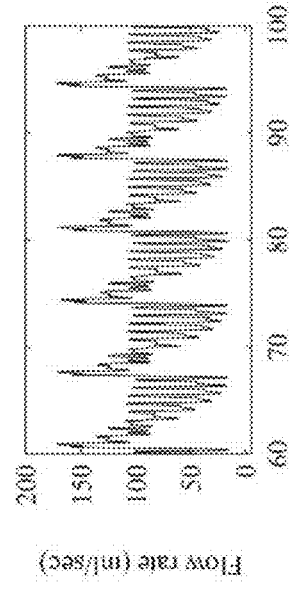
FIG. 3G
FIG. 3K

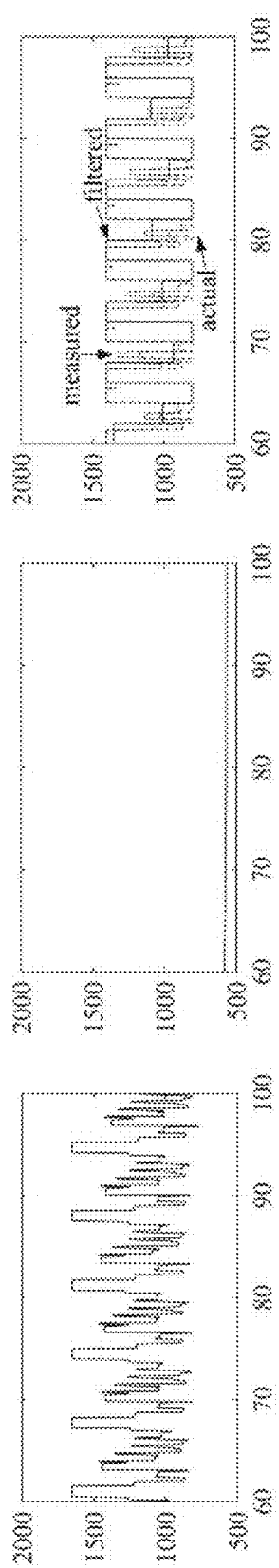
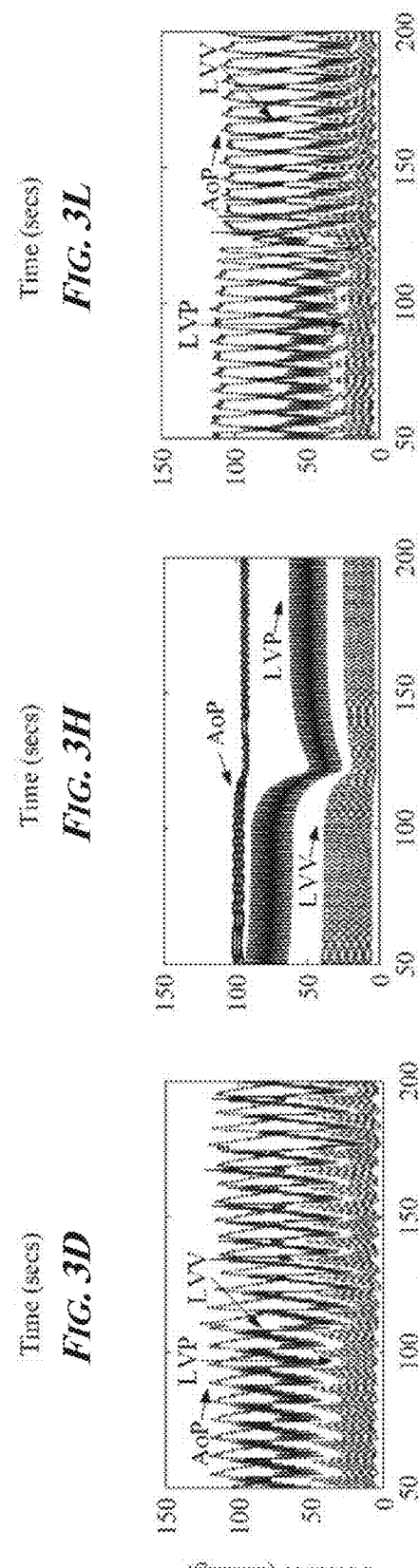
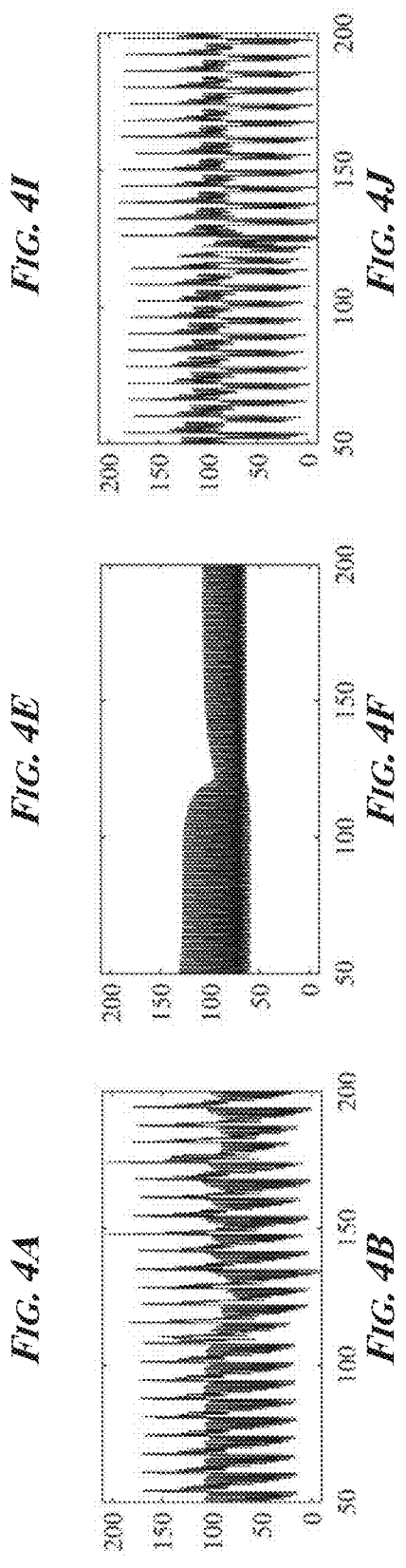
FIG. 3D, FIG. 3H, FIG. 3L, FIG. 4A, FIG. 4E, FIG. 4I, FIG. 4B, FIG. 4F, FIG. 4J

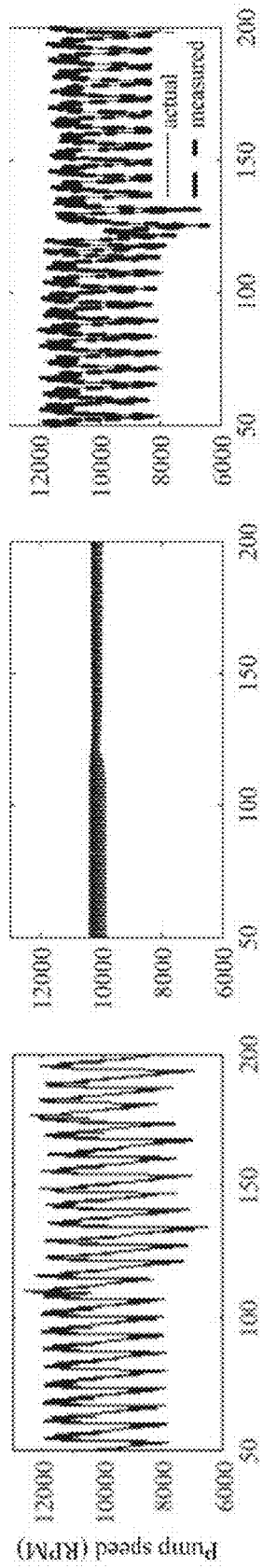
FIG. 4C
FIG. 4D
FIG. 5A
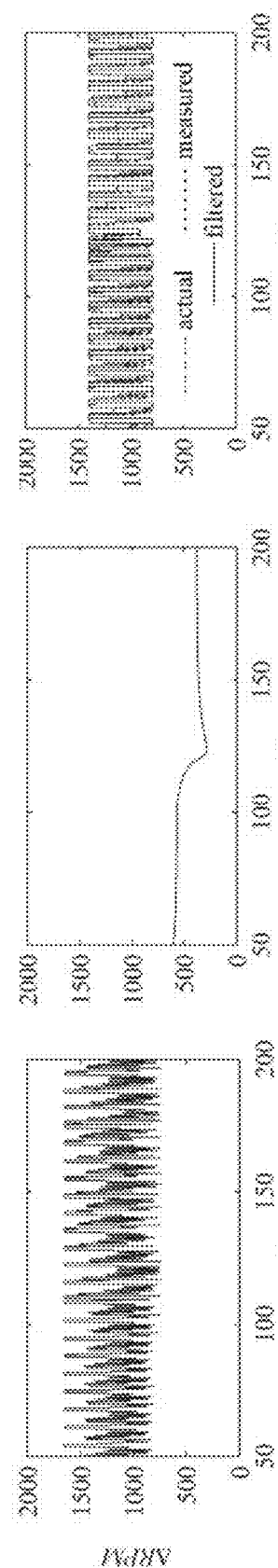
FIG. 4G
FIG. 4H
FIG. 5E
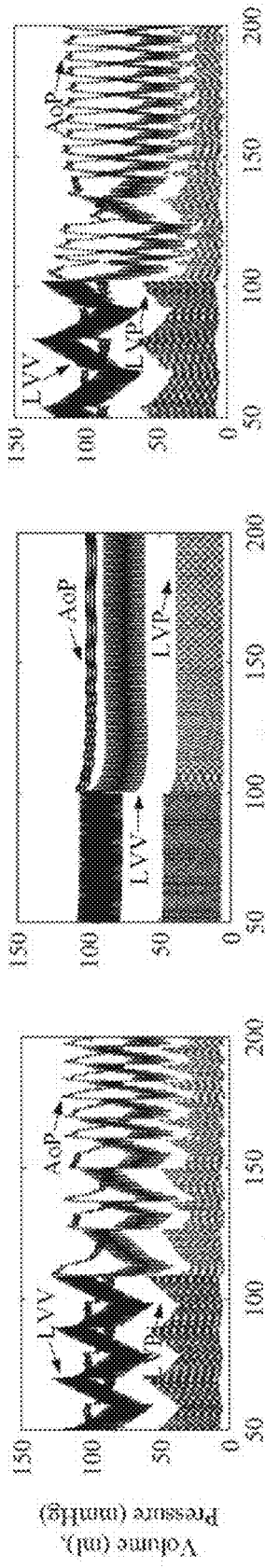
FIG. 4K
FIG. 4L
FIG. 5I

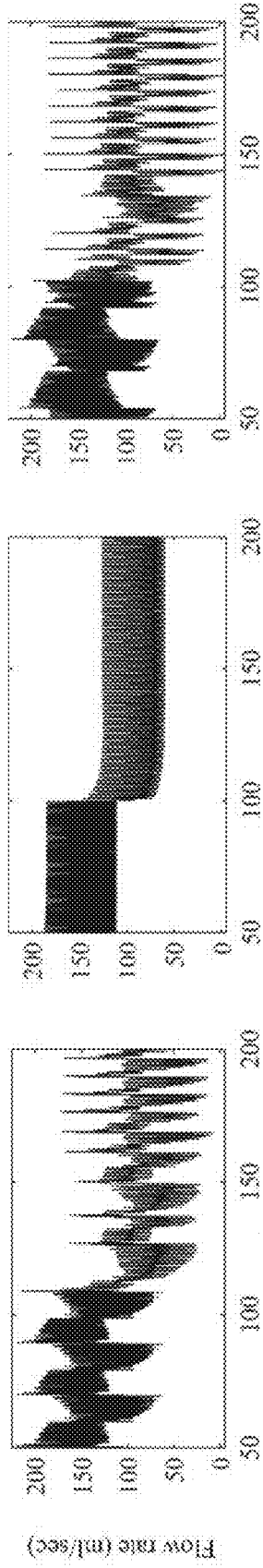
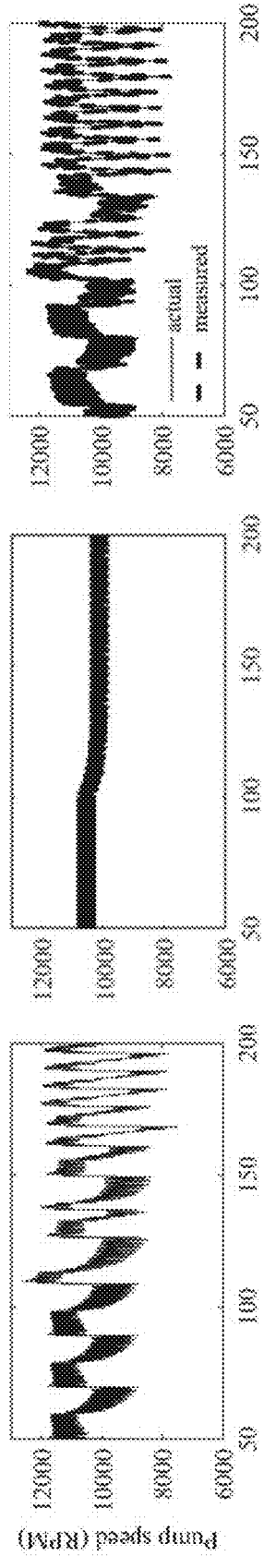
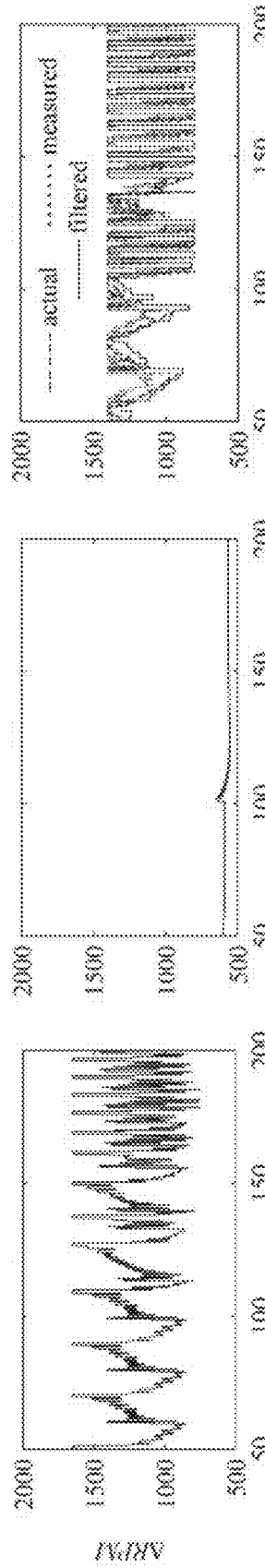
FIG. 5B  FIG. 5F  FIG. 5J
FIG. 5C  FIG. 5G  FIG. 5K
FIG. 5D  FIG. 5H  FIG. 5L

METHODS, SYSTEM, AND COMPUTER READABLE MEDIA FOR A ROTATIONAL SPEED-BASED CONTROL SYSTEM FOR VENTRICULAR ASSIST DEVICES

CROSS-REFERENCE TO RELATED APPLICATION

This application is based on and claims priority to U.S. Provisional Patent Application Ser. No. 62/757,377, filed Nov. 8, 2018, the disclosure of which is incorporated by reference herein in its entirety.

TECHNICAL FIELD

The presently disclosed subject matter relates primarily to the technology of controlling circulatory support devices. In some embodiments, the presently disclosed subject matter relates to the use of a rotational speed-based control system for ventricular assist devices (VADs).

BACKGROUND

Heart failure (HF) afflicts 6.5 million patients and is the leading cause of mortality in the United States. HF prevalence is expected to increase by 46% in 2030 to an estimated 8 million patients. In advanced HF, heart transplantation offers the best opportunity for long-term survival, but it is restricted to select patients based on multiple factors including age, co-morbidities, and end-organ function (Benjamin et al., 2017). Further, the number of available donor organs (~2000/year in the USA) cannot meet the growing demand (up to 30,000 per year). Mechanical circulatory support using left ventricular assist devices (LVAD) has emerged as standard clinical therapy for advanced heart failure due to the paucity of donor organs. LVADs are mechanical pumps that are implanted in patients to pump the blood from native left ventricle to the aorta to reduce ventricular workload and augment end-organ perfusion. With over 95% of total LVAD implants, and 80% survival rate at 1 year and 70% at 2 years (Kirklin et al., 2017), continuous flow (CF) LVADs are preferred over pulsatile flow (PF) LVADS due to their smaller size, simpler design, higher durability, and lower thrombosis rate (Cheng et al., 2014).

LVADs need to provide adequate blood flow to meet the perfusion demand, which frequently changes depending on clinical and physical activity conditions (physiologic perfusion), while simultaneously avoiding ventricular suction. Inadequate adaptation of pump flow can lead to hypoperfusion of end-organs, ventricular volume overload, pulmonary edema, and tissue hypoxia. Alternatively, over-pumping can result in ventricular suction. Ventricular suction occurs when the pump preload is reduced which causes reduced pressure in the ventricle. As a result, the ventricular wall occludes the LVAD inlet cannula. Suction events can cause myocardial damage, pump flow stoppage, or trigger ventricular arrhythmias that may result in adverse events or death (Sen et al., 2016). Physiologic perfusion and suction prevention are particularly challenging with CFLVADs due to: (1) non-linear nature of the circulatory system, (2) discontinuity in flows due to the presence of heart valves, (3) higher afterload and lower preload sensitivities of CFLVADs compared to the native heart (Khalil et al., 2008; Fukamachi et al., 2013), and (4) lack of biological sensors (e.g. baroreceptors) and biological feedback mechanisms (sympathetic and parasympathetic response, Frank Starling mechanism, etc.).

Currently, there are no physiologic control mechanisms incorporated into LVADs clinically. Physicians manually set the LVAD speed setpoints based on oxygen saturation, clinical symptoms, echocardiography, or estimated flows (Uriel et al., 2012; Uriel et al., 2013; Couperus et al., 2017).

Suction detection algorithms based on analysis of pump speed or pump current morphology are incorporated clinically, but these algorithms can only detect suction after it has occurred and cannot prevent suction (Vollkron et al., 2004; Voigt et al., 2005; Wang & Simaan, 2013). In the literature, multiple approaches for physiologic control and suction prevention have been proposed but these approaches need direct measurement of pressure, flow, and/or ventricular volume that requires the implantation of sensors (Stevens et al., 2011; Michael et al., 2014; Wang et al., 2018b). However, long-term direct measurement implantation of sensors is not desirable due to sensor drift, risk of sensor failure, thrombus formation, and septicemia. Further, sensors increase the overall cost and complexity of the system and reduce the overall reliability. To avoid implantation of sensors, model-based parameter estimation using the pump speed measurement using a variety of techniques (e.g. autoregressive exogenous, ARX modelling, and Extended Kalman Filters, EKF) have been proposed (Ayre et al., 2003; Giridharan & Skliar, 2006; Karantonis et al., 2007; Malagutti et al., 2007; Lim et al., 2008; AlOmari et al., 2009). However, model-based methods are susceptible to blood viscosity changes, friction forces and impeller inertia, and are computationally expensive to estimate pressure or flow. Flow estimators have been demonstrated to have significant errors clinically (Slaughter et al., 2009b) or may require the use of pressure sensors for higher accuracy (Pennings et al., 2013). Additionally, the model parameters have to be recalculated and validated for different pumps and small changes in pump geometry can lead to larger changes in pressure-flow relationship (Ayre et al., 2000). Notably, Petrou et al. recently explored the use of a machine learning model to predict blood viscosity during CFLVAD support (Petrou et al., 2018b), however, the method lacks validation in vivo, prone to learning sample errors, and increases complexity and computational cost on the controller. Approaches to alter pump design to increase the pressure sensitivity of rotary pumps have been proposed (Saxton & Andrews, 1960; Farrar et al., 2007; Frazier et al., 2010), but these design changes require lengthy and expensive FDA approval processes and may not be applicable universally.

Continuous flow (CF) LVADs have been widely accepted as a treatment option for advanced heart failure (HF) patients as a bridge to transplantation or as a destination therapy (Rose et al., 2001; Slaughter et al., 2009a). However, operating it at constant pump speeds reduces vascular pulsatility in the arteries of the patients (Stanfield et al., 2013; Patibandla et al., 2016; Soucy et al., 2017). There are clinical reports for some adverse events due to diminished vascular pulsatility during CFLVAD support at constant pump speeds, such as aortic insufficiency, arteriovenous malformations, gastrointestinal bleeding, hemorrhagic strokes, and valve fusion (Soucy et al., 2013a; Cheng et al., 2014). Comparatively, these events have not been often observed under pulsatile flow (PF) LVAD assistance (Frazier, 2010; Patibandla et al., 2016). Furthermore, non-pulsatile hemodynamics generated by long-term used CFLVAD leads to vascular structural and functional remodeling, such as morphologic changes in the aortic wall media, increase in aortic vascular stiffness, attenuation in peripheral endothelial function, and smooth muscle cell depletion (Segura et al., 2013; Ambardekar et al., 2015; Hasin et al., 2015; Amit et al., 2017; Ross et al., 2018). CFLVADs also reduced the pulmonary vascular resistance (PVR) less than Pulsatile Flow Left Ventricular Assist Devices (PFLVADs) in long-term assistance (Garcia et al., 2008). Another adverse effect of the reduced pulsatility under CFLVAD is that the coronary arteries developed marked remodeling with increased adventitial fibrosis (Ambardekar et al., 2018). The benefits of PF-LVAD over CFLVAD are summarized in Ündar, 2005 and Guan et al., 2010.

Considering the shortage of CFLVADs especially working at constant pump speeds, the open-loop control strategies to increase vascular pulsatility have been reported. Some of them regulated the pump flow under the condition of providing required cardiac output by using trapezoid wave, sinusoidal synchronization, and sequential flow modulation, to generate obvious vascular pulsatility (Vandenberghe et al., 2005; Cox et al., 2009; Ising et al., 2011). In comparison, the proposed pump speed modulation method guaranteed the average pump speed and adjusted the amplitude and frequency of the pump speed, which is synchronized and asynchronized with the cardiac cycle to achieve the augmentation of vascular pulsatility. Flow and speed modulation algorithms for CFLVADs have been used in the LVAD and total artificial heart (TAH; Fukamachi et al., 2010; Amacher et al., 2013; Jahren et al., 2014; Ising et al., 2015; Soucy et al., 2015). However, these methods were unable to consistently provide adequate perfusion over a wide range of clinical and physical activity scenarios.

Compared to the open-loop methods, the close-loop feedback control algorithms have been suggested to solve the limitation of open-loop control strategies for CFLVADs to enhance vascular pulsatility (Griffith et al., 2001; Choi et al., 2007; Gao et al., 2012; Bozkurt et al., 2014; Huang et al., 2014), while providing sufficient cardiac output. However, some algorithms focused on preventing phenomena of ventricular suction and backflow, resulting in limited increase in vascular pulsatility. Others needed implantation of pressure or flow sensors, which may not be reliable for clinically long-term use due to septicemia, pump thrombus, and possible sensor failure or drift (Giridharan & Skliar, 2006; Pauls et al., 2016).

Thus, herein disclosed in some embodiments is a simple and novel control algorithm based on the intrinsic pump speed which can be measured using phase current, does not deteriorate, and does not require any model estimations. In some embodiments, the control algorithm is based only on maintaining a set differential pump speed (ΔRPM) at a physiological, user-defined value, can simultaneously provide adequate perfusion and suction prevention during various physical activities. Also disclosed is a feedback control system under an axial CFLVAD support in-silico using a gain-scheduled, proportional-integral (PI) controller that maintains a higher and lower pump speed differentials ($\Delta RPM_H/\Delta RPM_L$) close to their corresponding user-defined thresholds ($\Delta RPM_{H'}/\Delta RPM_{L'}$), in order to effectively mimic the physiologic arterial pulsatility, while also maintaining an average cardiac output and implementing avoidance of ventricular suction under a wide range of physiologic conditions.

SUMMARY

This Summary lists several embodiments of the presently disclosed subject matter, and in many cases lists variations and permutations of these embodiments of the presently disclosed subject matter. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this Summary or not. To avoid excessive repetition, this Summary does not list or suggest all possible combinations of such features.

The presently disclosed subject matter in some embodiments relates to methods for controlling ventricular assist devices. In some embodiments, the methods comprise receiving at least one reference pump speed differential associated with a pump of a ventricular assist device; determining a filtered or non-filtered pump speed differential associated with the pump of a ventricular assist device; and adjusting, using a feedback based controller algorithm, current or power to the pump based on the at least one reference pump speed differential and the filtered pump speed differential. In some embodiments, the feedback based controller algorithm includes a proportional controller algorithm, a proportional-integral controller algorithm, a proportional-integral-derivative controller algorithm, a proportional-derivative controller algorithm, a fuzzy logic algorithm, an optimal control algorithm, or other control algorithm. In some embodiments, determining a filtered pump speed differential includes determining an average rotational pump speed differential over a period of time. In some embodiments, the filtered pump speed differential is based on multiple measurements using a phase current sensor or a hall effect sensor. In some embodiments, determining the filtered pump speed differential and adjusting the current to the pump is performed without using a pressure sensor, without using a priori pump model estimation, and/or without using a flow sensor. In some embodiments, the pump is an axial flow pump powered by a brushless direct current motor or any other type of motor. In some embodiments, adjusting, using the feedback based controller algorithm, current or power to the pump based on the at least one reference pump speed differential and the filtered pump speed differential includes alternating between a first reference pump speed differential and a second reference pump speed differential of the at least one reference pump speed as input to the feedback based controller algorithm so as to induce pulsatility, wherein the second reference pump speed differential is different than the first reference pump speed differential. In some embodiments, the presently disclosed methods comprise detecting that the average filtered pump speed differential or average filtered pump speed meets or is below at least one safe mode activation threshold value; and in response to detecting the average filtered pump speed differential or average filtered pump speed meets or is below the at least one safe mode activation threshold value, triggering a safe mode for the pump, whereby the pump is set to maintain a constant pump speed. In some embodiments, the safe mode is triggered during ventricular fibrillation, left ventricular asystole, arrhythmia, or other adverse cardiac event. In some embodiments, the at least one safe mode activation threshold value includes a predetermined average filtered pump speed differential or average filtered pump speed value being detected for longer than a user-defined period of time. In some embodiments, the ventricular assist device includes a continuous flow right ventricular assist device (CFRVAD), a continuous flow left ventricular assist device (CFLVAD), or a continuous flow ventricular assist device (CFVAD).

The presently disclosed subject matter in some embodiments also relates to systems for controlling ventricular assist devices. In some embodiments, the systems comprise a non-transitory computer readable medium; and a controller implemented using the non-transitory computer readable medium, wherein the controller is configured for receiving at least one reference pump speed differential associated with a pump of a ventricular assist device; determining a filtered pump speed differential associated with the pump of a ventricular assist device; and adjusting, using a feedback based controller algorithm, current to the pump based on the at least one reference pump speed differential and the filtered pump speed differential. In some embodiments, the feedback based controller algorithm includes a proportional controller algorithm, a proportional-integral controller algorithm, a proportional-integral-derivative controller algorithm, a proportional-derivative controller algorithm, a fuzzy logic algorithm, an optimal control algorithm, or other control algorithm. In some embodiments, determining a filtered pump speed differential includes determining an average rotational pump speed differential over a period of time. In some embodiments, the filtered pump speed differential or pump speed differential is based on multiple measurements using a phase current sensor or a hall effect sensor. In some embodiments, the controller is configured for determining the filtered pump speed differential and adjusting the current to the pump without using a pressure sensor, without using a priori pump model estimation, and/or without using a flow sensor. In some embodiments, the pump is an axial flow pump powered by a brushless direct current motor or any other type of motor. In some embodiments, the controller is configured for alternating between a first reference pump speed differential and a second reference pump speed differential of the at least one reference pump speed differential as input to the feedback based controller algorithm so as to induce pulsatility, wherein the second reference pump speed differential is different than the first reference pump speed. In some embodiments, the controller is further configured for detecting that the average filtered pump speed differential or average filtered pump speed meets or is below at least one safe mode activation threshold value; and in response to detecting the average filtered pump speed differential or average filtered pump speed meets or is below the at least one safe mode activation threshold value, triggering a safe mode for the pump, whereby the pump is set to maintain a constant pump speed. In some embodiments, the safe mode is triggered during ventricular fibrillation, left ventricular asystole, arrhythmia, or other adverse cardiac event. In some embodiments, the at least one safe mode activation threshold value includes a predetermined average filtered pump speed differential or average filtered pump speed value being detected for longer than a user-defined period of time. In some embodiments, the ventricular assist device includes a continuous flow right ventricular assist device (CFRVAD), a continuous flow left ventricular assist device (CFLVAD), or a continuous flow ventricular assist device (CFVAD).

The presently disclosed subject matter in some embodiments also relates to non-transitory computer readable media having stored thereon executable instructions that when executed by at least one processor of a computer cause the computer to perform steps comprising receiving at least one reference pump speed or pump speed differential associated with a pump of a ventricular assist device; determining a filtered pump speed differential associated with the pump of a ventricular assist device; and adjusting, using a feedback based controller algorithm, current to the pump based on the at least one reference pump speed differential and the filtered pump speed differential. In some embodiments, the feedback based controller algorithm includes a proportional controller algorithm, a proportional-integral controller algorithm, a proportional-integral-derivative controller algorithm, a proportional-derivative controller algorithm, a fuzzy logic algorithm, an optimal control algorithm, or other control algorithm. In some embodiments, the ventricular assist device includes a continuous flow right ventricular assist device (CFRVAD), a continuous flow left ventricular assist device (CFLVAD), or a continuous flow ventricular assist device (CFVAD).

The presently disclosed subject matter in some embodiments also relates to methods for controlling ventricular assist devices comprising receiving at least one reference pump parameter differential associated with a pump of a ventricular assist device; determining a filtered or non-filtered pump parameter differential associated with the pump of a ventricular assist device; and adjusting, using a feedback based controller algorithm, current or power to the pump based on the at least one reference pump parameter differential and the filtered pump parameter differential. In some embodiments, the feedback based controller algorithm includes a proportional controller algorithm, a proportional-integral controller algorithm, a proportional-integral-derivative controller algorithm, or a proportional-derivative controller algorithm. In some embodiments, the pump parameter includes pump current, pump power, and/or pump flow rate. In some embodiments, the ventricular assist device includes a continuous flow right ventricular assist device (CFRVAD), a continuous flow left ventricular assist device (CFLVAD), or a continuous flow ventricular assist device (CFVAD).

BRIEF DESCRIPTION OF THE FIGURES

FIGS. 3A-3L are a series of graphs of simulated hemodynamic waveforms of left ventricular pressure (LVP), volume (LVV), and aortic pressure (AoP) and pump parameters (flow rate, speed, and $\Delta RPM$) for a failing hear at rest. Shown are the waveforms with a sensor-based control algorithm (FIGS. 3A-3D), a constant RPM control algorithm (FIGS. 3E-3H), and an exemplary sensorless control algorithm of the presently disclosed subject matter (FIGS. 3I-3L).

FIGS. 4A-4L are a series of graphs of simulated hemodynamic waveforms of left ventricular pressure (LVP), volume (LVV), and aortic pressure (AoP) and pump parameters (flow rate, speed, and $\Delta RPM$) for a failing hear at rest for 5-fold increased pulmonary vascular resistance (PVR) with a sensor-based control algorithm (FIGS. 4A-4D), a constant RPM control algorithm (FIGS. 4E-4H), and an exemplary sensorless control algorithm of the presently disclosed subject matter (FIGS. 4I-4L). The increase in PVR was initiated at t=100 seconds while $\Delta RPM_{Hr}$ was held with the exemplary algorithms of the presently disclosed subject matter and t=100 seconds with constant RPM control algorithm.

FIGS. 5A-5L are a series of graphs of simulated hemodynamic waveforms of left ventricular pressure (LVP), volume (LVV), and aortic pressure (AoP) and pump parameters (flow rate, speed, and ΔRPM) for a failing hear at rest during a step-down transition from exercise to rest with a sensor-based control algorithm (FIGS. 5A-5D), a constant RPM control algorithm (FIGS. 5E-5H), and an exemplary sensorless control algorithm of the presently disclosed subject matter (FIGS. 5I-5L). The transition was initiated at t was around 100 seconds when $\Delta RPM_{Lr}$ with the exemplary algorithms of the presently disclosed subject matter and at t=100 seconds with the constant RPM control algorithm.

DETAILED DESCRIPTION

Figure 1:
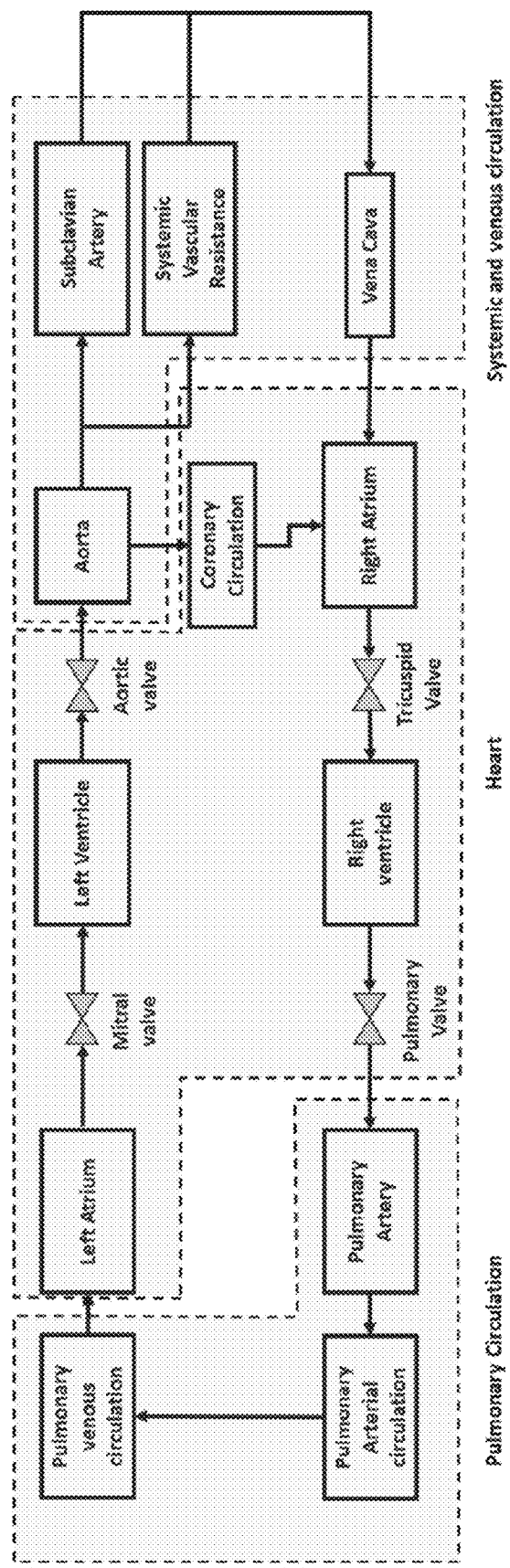
FIG. 1 is a schematic representation of an exemplary nonlinear mathematical model employed in the presently disclosed subject matter. The cardiovascular system is simulated using twelve lumped blocks, each is defined by a resistance and a compliance. The instantaneous volume is calculated using differential Equation (2) below.

Continuous flow left ventricular assist devices (CFLVADs) are currently operated at a fixed pump speed in the clinic, which cannot provide sufficient physiologic perfusion over a wide range of physical activities, diminishes vascular pulsatility, and is susceptible to ventricular suction. Disclosed herein are control strategies for CFLVAD that meet the objectives of physiologic perfusion and suction prevention, while simultaneously augmenting vascular pulsatility. Furthermore, the control algorithms disclosed herein do not require pressure, flow, or volume sensors that are prone to failure and baseline drift during the long-term use and do not require complicated model-based estimations of pressures and flow or pump parameters.

The presently disclosed algorithms employ the intrinsic pump parameter of pump speed to calculate the differential pump speed (ΔRPM) over a 2-second time window. The control algorithms work to maintain the measured ΔRPM at a selected reference setpoint, thereby achieving both objectives of physiologic perfusion and suction prevention. To augment arterial pulsatility, a gain-scheduled, proportional-integral controller can be used to maintain the ΔRPM at a low ΔRPM setpoint ($\Delta RPM_{Lr}$), leading to high LVAD flow. When the ΔRPM reduces as the native ventricle is unloaded, the controller automatically switches to a high ΔRPM setpoint ($\Delta RPM_{Hr}$) that reduces LVAD flow and the controller will switch continuously between the two ΔRPM setpoints ($\Delta RPM_{Hr}/\Delta RPM_{Lr}$) to generate pulsatility. Efficacy and robustness of the algorithms of the presently disclosed subject matter were evaluated in-silico during simulated rest and exercise test conditions, transition from exercise to rest, a rapid (<20 second) eight-fold increase in pulmonary vascular resistance and five-fold increase in pulmonary vascular resistance (PVR) with pulse flow modulation, and different levels of noise in measured pump speed. Pump independency was demonstrated by successfully applying the control algorithms disclosed herein in silico using mathematical models of an axial flow pump (Heartmate II), and mixed flow pump (Deltastream DP2).

The control algorithms disclosed herein maintained adequate physiologic perfusion while avoiding ventricular suction for all test conditions, including measurement noise and a rapid increase in PVR. The control algorithms disclosed herein augmented vascular pulsatility by generating aortic pressure variation of about 40 mmHg at rest and 30 mmHg during exercise at a frequency of 3-10 cycles per minute.

As such, the presently disclosed control algorithms demonstrated feasibility and robustness, and successfully predicted its function and efficacy over the wide range of expected clinical test conditions.

I. DEFINITIONS

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques or substitutions of equivalent techniques that would be apparent to one of skill in the art. While the following terms are believed to be well understood by one of ordinary skill in the art, the following definitions are set forth to facilitate explanation of the presently disclosed subject matter.

While the following terms are believed to be well understood by one of ordinary skill in the art, the following definitions are set forth to facilitate explanation of the presently disclosed subject matter.

As used herein, the term "node" refers to a physical computing platform or device including one or more processors and memory.

As used herein, the term "module" refers to hardware, firmware, or software in combination with hardware and/or firmware for implementing features described herein.

As used herein and in the appended claims, the singular forms "a," "an," and "the" include plural referents unless the context clearly dictates otherwise. For example, a processor refers to one or more processor. As such, the terms "a", "an", "one or more" and "at least one" can be used interchangeably. Similarly, the terms "comprising", "including" and "having" can be used interchangeably. It is further noted that the claims may be drafted to exclude any optional element. As such, this statement is intended to serve as antecedent basis for use of such exclusive terminology as "solely," "only" and the like, in connection with the recitation of claim elements, or use of a "negative" limitation.

Ranges can be expressed herein as from "about" one particular value, and/or to "about" another particular value. When such a range is expressed, some embodiments includes from the one particular value and/or to the other particular value. Similarly, when values are expressed as approximations, by use of the antecedent "about," it will be understood that the particular value forms an embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed, then "less than or equal to 10" as well as "greater than or equal to 10" are also disclosed. It is also understood that the throughout the application, data are provided in a number of different formats, and that these data represent in some embodiments endpoints and starting points and in some embodiments ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

The term "and/or", when used in the context of a list of entities, refers to the entities being present singly or in combination.

The terms "optional" and "optionally" as used herein indicate that the subsequently described event, circumstance, element, and/or method step may or may not occur and/or be present, and that the description includes instances where said event, circumstance, element, or method step occurs and/or is present as well as instances where it does not.

II. EXEMPLARY EMBODIMENTS

The presently disclosed subject matter relates in some embodiments to the use of a rotational differential speed-based control system for ventricular assist devices (VADs). As disclosed herein, the presently disclosed subject matter involves multiple aspects, including but not limited to: (1) a controller apparatus or system and/or a related algorithm for controlling a VAD using pump speed differential, pump current differential, or pump flow differential to provide physiologic perfusion and prevent ventricular suction (e.g., using the measurement of intrinsic pump speed, eliminating the need for implantable sensors or model-based estimation methods); (2) a safe mode to maintain a constant pump speed in the event of ventricular fibrillation or left ventricular asystole (e.g., to maintain pump flows at basal levels (heart failure baseline) to potentially sustain life while avoiding pump thrombosis and suction); (3) a feedback based methodology to artificially create physiologic pulse pressure and flow pulsatility while maintaining physiologic perfusion and avoiding suction In some embodiments of the presently disclosed subject matter, an algorithm may be implemented in a controller or related device (e.g., a programmable logic device or other suitable entity containing hardware and/or software, e.g., a processor and/or memory). For example, a continuous flow left VAD or related pump controller may be configured, via suitable programming, for receiving a reference pump speed differential associated with a pump of a ventricular assist device; determining a filtered pump speed differential associated with the pump of a ventricular assist device; and adjusting, using a feedback based controller algorithm (e.g., a proportional controller algorithm, a proportional-integral controller algorithm, a proportional-integral-derivative controller algorithm, a proportional-derivative controller algorithm, or other types of control algorithms (e.g., fuzzy logic, optimal control, etc.), current to the pump based on the reference pump speed differential and the filtered pump speed differential. In this example, by adjusting the current to the pump, the controller may adjust the rotational speed of the pump in effort to achieve and/or maintain the reference pump speed differential (e.g., the reference pump speed or pump speed differential may be selected or determined by a physician or other healthcare provider and/or may be deemed the ideal pump speed for a given patient based on a variety of factors).

In some embodiments, a continuous flow left VAD or related pump controller may be configured, via suitable programming, for receiving a reference pump parameter (e.g., current, power, speed, flow) differential associated with a pump of a ventricular assist device; determining a filtered pump parameter differential associated with the pump of a ventricular assist device; and adjusting, using a feedback based controller algorithm, current to the pump based on the reference pump parameter differential and the filtered pump parameter differential. In some embodiments, by adjusting the current to the pump, the controller may adjust the rotational speed of the pump in effort to achieve and/or maintain the reference pump parameter differential (e.g., the reference pump current differential may be selected or determined by a physician or other healthcare provider and/or may be based on a variety of relevant factors). In some embodiments, the pump parameter used by the controller may be selected from the group consisting of pump current, pump power, pump speed, and pump flow rate. In some embodiments, the differential is calculated over a time period of part of a cardiac cycle or multiple cardiac cycles.

In some embodiments, a continuous flow left or right VAD may be operated to augment pulsatility by alternating between two different setpoints for pump speed differential. The related pump controller may be configured, via suitable programming, for receiving a first reference pump speed differential (e.g., 800 rotations per minute (RPM)) and a second reference pump speed differential (e.g., 1700 RPM) associated with a pump of a ventricular assist device; determining a filtered pump speed differential associated with the pump of a ventricular assist device; and adjusting, using a feedback based controller algorithm, current to the pump based on the reference pump speed differentials and the filtered pump speed differential. In some embodiments, the controller may alternate between the two reference pump speed differentials when computing the adjustment to the pump current using the controller algorithm, thereby inducing pulsatility. In some embodiments, by adjusting the current to the pump, the controller may adjust the rotational speed of the pump in effort to achieve and/or maintain the reference pump speed differential.

Figure 6:
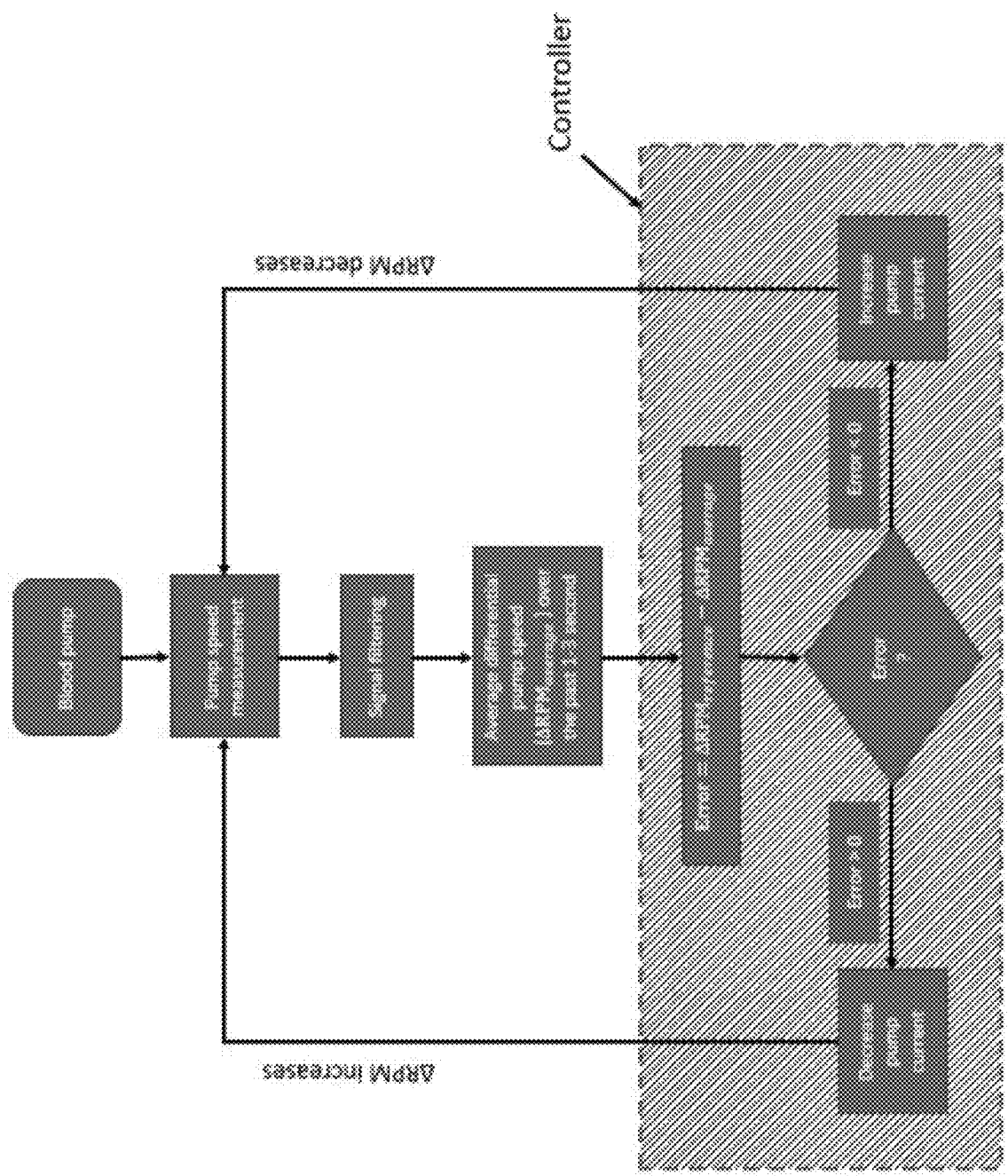
FIG. 6 is a flow chart of an exemplary ΔRPM control strategy of the presently disclosed subject matter, $\Delta RPM_{ref}$ the reference high or low differential pump speed.

FIG. 6 depicts an exemplary flow chart for a control strategy using aspects described herein. In FIG. 6, pump speed measurement step 602 associated with a VAD may be obtained. Using signal filtering step 604, average differential pump speed 606 over a time period (e.g., the past one—three seconds or greater) may be determined. VAD controller or related pump controller 603 may use a feedback based controller algorithm to adjust pump speed by changing current to blood pump 601. For example, the feedback based controller algorithm may determine the difference (represented as Error 601 in FIG. 6) between a reference pump speed differential and the measured pump speed differential in step 608. Depending on the results, the controller may decrease the pump current (e.g., if error is more than zero; step 612) or the controller may increase the pump current (e.g., if error is less than zero; step 614).

The subject matter described herein can be implemented in software in combination with hardware and/or firmware. For example, the subject matter described herein can be implemented in software executed by a processor. In one exemplary implementation, the subject matter described herein may be implemented using a computer readable medium having stored thereon computer executable instructions that when executed by the processor of a computer control the computer to perform steps. Exemplary computer readable media suitable for implementing the subject matter described herein include non-transitory devices, such as disk memory devices, chip memory devices, programmable logic devices, and application specific integrated circuits. In addition, a computer readable medium that implements the subject matter described herein may be located on a single device or computing platform or may be distributed across multiple devices or computing platforms.

It should be noted that a controller, a VAD, and/or functionality described herein may constitute a special purpose computing device. Further, a controller, a VAD, and/or functionality described herein can improve the technological fields of VADs and related devices. For example, by using measurements of a pump parameter (e.g., rotational speed of a brushless direct current motor) and a related reference pump parameter differential to control a pump of a VAD, a controller can effectively control a VAD without needing implantable sensors or model-based estimation method, and whereby the VAD can provide physiologic perfusion and prevent ventricular suction. In this example, the pump parameter may include pump current, pump power, and/or pump flow rate. In some examples where pump flow rate is a pump parameter used by a controller to control a VAD, one or more implantable sensors may be used in detecting pump flow rate.

EXAMPLES

The following Examples provide illustrative embodiments. In light of the present disclosure and the general level of skill in the art, those of skill will appreciate that the following Examples are intended to be exemplary only and that numerous changes, modifications, and alterations can be employed without departing from the scope of the presently disclosed subject matter.

Materials and Methods for the Examples

Modeling of the Human Circulatory System.

This study was implemented using an updated computer simulation model of the human circulatory system in HF. The model with previous versions has been validated and adopted to develop and evaluate different physiologic control, timing, and fault detection methods for different mechanical circulatory support (MCS) devices (Giridharan et al., 2002; Giridharan et al., 2006; Ising et al., 2011; Soucy et al., 2013b). The human circulatory model was divided into four heart valves and twelve lumped parameter blocks, and each block has been characterized by a resistance factor as zero volume and a storage factor as zero resistance to flow. The twelve blocks are right atria (RA), right ventricle (RV), pulmonary artery, pulmonary arterial, pulmonary vein, left atria (LA), left ventricle (LV), aorta, systemic circulation, vena cava, coronary artery, and subclavian artery (see FIG. 1). The RA, RV, LV, and RV were characterized by four nonlinear, time-varying compliances. The coronary artery block consisted of time-varying resistance and compliance elements. The remaining blocks were not characterized with time-varying elements. Moreover, the blood volume in each block was described by the following differential equations as a function of volume (V), pressure (P), compliance (C), and resistance (R):

$$\frac{dV_n}{dt} = F_n^{in} - F_n^{out} \tag{1}$$

Substituting $$C_n = \frac{V_n}{P_n} \text{ and } F_n^{in} = \frac{P_{n-1} - P_n}{R_{n-1}} \text{ and } F_n^{out} = \frac{P_n - P_{n+1}}{R_n}$$

into (1) results in:

$$\frac{dV_n}{dt} = \frac{V_{n-1}}{C_{n-1}R_{n-1}} - \frac{V_n}{C_n}\left(\frac{1}{R_{n-1}} + \frac{1}{R_n}\right) + \frac{V_{n+1}}{C_{n+1}R_n} \tag{2}$$

where $dV_n/dt$ is the rate of volume change in block n, $F_n^{in}$ is the blood flow rate into block n, $F_n^{out}$ is the blood flow rate out of block n.

Modeling of the Axial CFLVAD.

In this study, the human circulatory model in HF was integrated with a parameter-based axial CFLVAD model, which was developed by Choi (Choi et al., 1997). The axial CFLVAD was driven by a brushless DC motor, described by the following equation (Pillay & Krishnan, 1989):

$$J\frac{d\omega}{dt} = \frac{3}{2}K_B I - B\omega - a_0\omega^3 - a_1 F_p \omega^2 \tag{3}$$

where J is the inertia of the rotor, ω is the rotor speed in rad/s, $K_B$ is the back electromotive force (EMF) constant, I is the pump current, B is the damping coefficient, $a_0$ and $a_1$ are correlation constants. In addition, $F_p$ is LVAD flow rates, whose differential expression in terms of pump speed (ω) and pressure difference across the pump (ΔP) was given as follows (Konishi et al., 1994; Choi et al., 1997):

$$\frac{dF_p}{dt} = -\frac{b_0}{b_1}F_p - \frac{b_0}{b_1}\omega^2 + \frac{1}{b_1}\Delta P \tag{4}$$

where $b_0$, $b_1$, and $b_2$ are experimental constants. Parameters in equation (4) are experimentally characterized as J=9.16×$10^{-7}$ kg m$^2$, $K_B$=0.003, B=6.6×$10^{-7}$ kg m$^2$/s, $a_0$=7.38×$10^{-13}$ kg m$^2$ s/ml$^3$, $a_1$=1.98×$10^{-11}$ kg m$^2$ s/ml, $b_0$=−0.296 mmHg s/ml, $b_1$=−0.027 mmHg s$^2$/ml, and $b_2$=9.33×$10^{-5}$ mmHg s$^2$ (Choi et al., 1997). The equation parameters are experimentally characterized and given as J=9.16×$10^{-7}$ kg m$^2$, $K_B$=0.003, B=6.6×$10^{-7}$ kg m$^2$/s, $a_0$=7.38×$10^{-13}$ kg m$^2$ s/ml$^3$, $a_1$=1.98×$10^{-11}$ kg m$^2$ s/ml, $b_0$=−0.296 mmHg s/ml, $b_1$=−0.027 mmHg s$^2$/ml, and $b_2$=9.33×$10^{-}$ mmHg s$^2$.

The axial CFLVAD was integrated into the human circulatory system model (FIG. 2) as parallel flow paths from the LV to the aorta. The combination of the axial CFLVAD and the circulatory system models only affected the LV and aorta differential equations.

An Exemplary Feedback Control System for the Axial CFLVAD.

Figure 2:
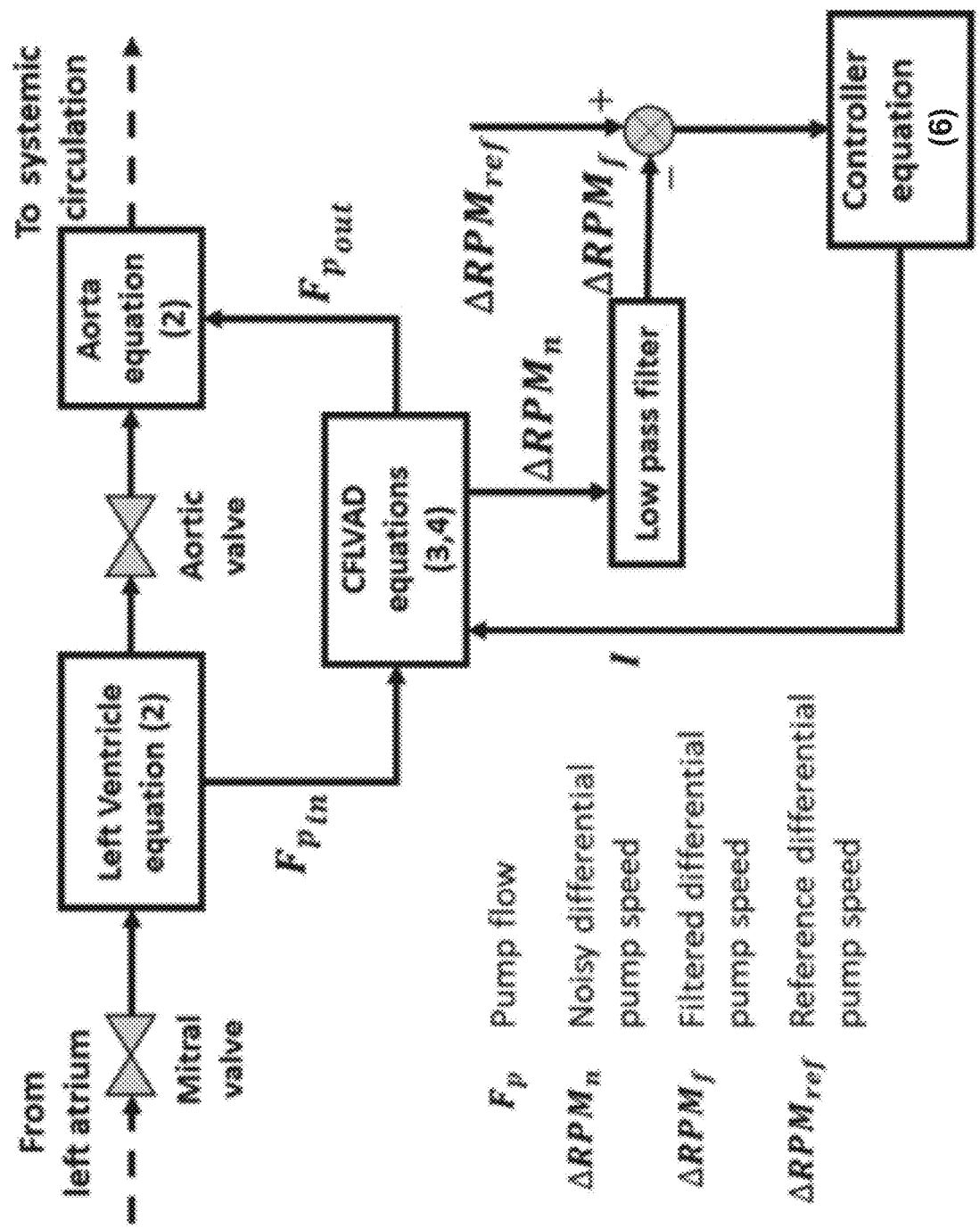
FIG. 2 is a schematic of an exemplary control algorithm of the presently disclosed subject matter. It employs two gain-scheduled, proportional-integral (PI) controllers that maintain a higher and lower pump speed differentials ($\Delta RPM_H/\Delta RPM_L$) close to their corresponding user-defined thresholds ($\Delta RPM_{Hr}/\Delta RPM_{Lr}$), where $\Delta RPM_{ref}$ is the reference high or low differential pump speed. CFLVAD: continuous flow left ventricular assist device.

The control objectives of the proposed algorithm were to maintain the higher pump speed differential ($\Delta RPM_H$) below the specified reference setpoint ($\Delta RPM_{Hr}$), and maintain the lower pump speed differential ($\Delta RPM_L$) above the specified reference setpoint ($\Delta RPM_{Lr}$), to generate adequate vascular pressure, while providing sufficient physiologic perfusion and avoiding ventricular suction. In this study, $\Delta RPM_{Hr}$ and $\Delta RPM_{Lr}$ were calculated without and with noisy pump speed measurements (FIG. 2). Noisy pump speed measurements were obtained by adding a 1% uniformly distributed noise to the simulated values of pump speed at a 100 Hz sampling rate. The noisy measurements were conditioned using a low pass Butterworth filter with a 5 Hz cutoff frequency. The control objectives were satisfied by implementing a gain-scheduled PI controller that switches between $\Delta RPM_{Lr}$ and $\Delta RPM_{Hr}$ (when $\Delta RPM_L$ was above and close to $\Delta RPM_{Lr}$ then the reference $\Delta RPM$ is to $\Delta RPM_{Hr}$, or when $\Delta RPM_H$ was below and close to $\Delta RPM_{Hr}$ then the reference $\Delta RPM$ is to $\Delta RPM_{Lr}$), to satisfy the objectives of increasing vascular pulsatility, generating sufficient physiologic perfusion, and simultaneously preventing suction. This fixed controller configuration only requires the selection of controller coefficients and setpoints of target pump speed differentials. The pump motor current (I) was updated based on the following control law:

$$I = -[k_1(\Delta RPM_r - \Delta RPM) + k_2(\int_0^t (\Delta RPM_r - \Delta RPM) dt] \quad (5)$$

where $\Delta RPM_r$ is the referenced higher/lower pump speed differential, $\Delta RPM$ is the pump speed differential calculated directly (sensor-based) or from low-pass filtered pump speed measurements (sensorless), $k_1$ and $k_2$ are user defined gain scheduled controller coefficients.

The schematic of the proposed control algorithm is shown in FIG. 2.

Efficacy and robustness of the proposed strategy was evaluated during simulated rest and exercise test conditions for (1) sensor-based $\Delta RPM$; (2) sensorless $\Delta RPM$; (3) a five-fold increase in PVR through (1) and (2). The simulated heart rate was 80 beats per minute (bpm) during rest and 120 bpm during exercise. Before t=0, unassisted perfusion was assumed. At time t=0 (arbitrarily selected as the end of the diastole), CFLVAD support was initiated with the reference differential pump speeds ($\Delta RPM_{Lr}$=750 RPM, $\Delta RPM_{Hr}$=1650 RPM for the sensor-based method, $\Delta RPM_{Lr}$=800 RPM, $\Delta RPM_{Hr}$=1400 RPM for the sensorless method) sent to the PI CFLVAD controller. The actual $\Delta RPM$ was the difference between the maximum and minimum RPM as directly calculated for the sensor-based algorithm or low-pass filtered during the preceding two-second time period (moving two-second time window) for the sensorless algorithm, irrespective of simulated native heart rate. The selected values for $k_1$ and $k_2$ were unchanged during all test conditions for sensor or sensorless based strategy but slightly changed between the two algorithms. Initial LVAD flow rate and RPM were set to zero. The simulation was continued up to 300 seconds. The mean values of pressures, flows, and volumes were reported when the waveforms were stable. The performance of the proposed sensorless algorithm was compared to (1) the performance of the sensor-based algorithm when $\Delta RPM$ was directly measured without any measurement noise, (2) the performance of control algorithm with constant RPM averaged with the actual pump speed.

Pump Independency.

To show pump independency, the $\Delta RPM$ controller was implemented using a Deltastream mixed flow Pump (DP2; Medos AG, Stolberg, Germany). For the DP2 pump, the pump model was based largely on Petrou et al., 2018a. The pump equations for the DP2 pump are:

$$\frac{d\omega}{dt} = \frac{1}{J(\omega)}(K_T - g_1(\omega) + g_2\omega - g_3\omega^2 - g_4 F_P\omega) \text{ and} \quad (6)$$

$$\frac{dF_P}{dt} = -\frac{1}{F}(-\Delta P + f_1\omega^2 - f_2 F_P - f_3 F_P^2) \quad (7)$$

where $f_1$, $f_2$, $f_3$, $K_T$, $g_1(\omega)$, $g_2$, $g_3$, $g_4$, $J(\omega)$, and F are coefficients defined as follows:

| | | | |
|---|---|---|---|
| $f_1$ | $6.572 \times 10^{-6} \frac{mmHg}{RPM^2}$ | F | $0.8596 \frac{mmHg}{\frac{L}{min}/s}$ |
| $f_2$ | $6.572 \times 10^{-6} \frac{mmHg}{L/min}$ | $g_2$ | $1.087 \times 10^{-10} \frac{Nm}{RPM}$ |
| $f_3$ | $6.572 \times 10^{-6} \frac{mmHg}{L/min^2}$ | $g_3$ | $3.280 \times 10^{-10} \frac{Nm}{RPM^2}$ |
| $K_T$ | $13 \times 10^{-3} \frac{Nm}{A}$ | $g_4$ | $2.629 \times 10^{-7} \frac{Nm}{\frac{L}{min} RPM}$ |
| $g_1(\omega)$ | $\begin{bmatrix} RPM & Nm \times 10^{-3} \\ 2000 & 3.563 \\ 3000 & 3.447 \\ 4000 & 3.480 \\ 5000 & 3.317 \\ 6000 & 3.264 \end{bmatrix}$ | $J(\omega)$ | $\begin{bmatrix} RPM & \frac{Nm}{RPM/2} \times 10^{-6} \\ 2000 & 1.444 \\ 3000 & 1.498 \\ 4000 & 1.560 \\ 5000 & 1.615 \\ 6000 & 1.723 \end{bmatrix}$ |

Data Analysis.

Hemodynamic parameter values and ventricular pressure-volume loop responses were calculated using m-files developed in MATLAB (MathWorks, Natick, Mass.). Pressure, flow, and volume waveforms were used to calculate the following hemodynamic parameters: cardiac output; aortic systolic, diastolic and mean pressures; left ventricular systolic, end diastolic, peak and minimum pressures and volumes; aortic, coronary artery, LVAD flows, and actual, filtered, and measured $\Delta RPM$ values. Vascular pulsatility was quantified using aortic pulse pressure. Characterizing hemodynamic parameters were calculated for all test conditions. Suction was defined to have occurred when the instantaneous ventricular pressure value was no larger than 1 mmHg (Simaan et al., 2009).

Sensorless Control of the CFLVAD.

An objective of the controllers of the presently disclosed subject matter is to maintain a fixed differential pump speed (ΔRPM) which produces sufficient perfusion at exercise and rest while avoiding suction events during reduced preload. In some embodiments, the controllers of the presently disclosed subject matter are based solely on the noisy measurements of pump speed, $\Delta RPM_n$, which can be based on phase currents or hall effect sensors. To achieve model-independent control, a moving average filter (window size=8 data points) was used for filtering the rotor speed measurement. Robustness analysis was achieved by introducing different levels of normally distributed noise (1%-100%) to the pump speed at 100-Hz sampling rate. A simple proportional-integral (PI) controller is used to maintain the differential pump speed setpoint by the following control law:

$$I = -K_P(\Delta RPM_{ref} - \Delta RPM_f) - \frac{K_P}{\tau}\int_0^t (\Delta RPM_{ref} - \Delta RPM_f)dt \quad (8)$$

where I is the pump current, $\Delta RPM_{ref}$ is the reference differential pump speed and $\Delta RPM_f$ is the filtered differential pump speed at any instant, $K_P$ and $\tau$ are the proportional and integral gains respectively. The negative sign in Equation (8) is due to the inverse relation between pump speed pulsatility and ventricular loading. High pump speed pulsatility implies low ventricular unloading and low pulsatility implies a high ventricular unloading. The PI-controller gains were tuned a priori using a direct numerical search approach disclosed in Ayre et al., 2000. $K_P$ was set to 0.00025, and $\tau$ was set to 5. $\Delta RPM_n$ was calculated as the difference between the maximum and minimum noisy RPM values during a moving time window of the preceding two seconds. $\Delta RPM_{ref}$ was set to 800 RPM. The control schematic is shown in FIG. 2 and is referred to herein as ΔRPM control. The performance of the ΔRPM control was compared with two sensorless and two sensor-based control algorithms.

Comparison with Sensorless Control Algorithms.

The disclosed ΔRPM algorithm was compared to two sensorless algorithms previously proposed: (1) a constant speed algorithm; and (2) a constant differential pressure, $\Delta P_d$ (pressure difference between left ventricle and aorta). Maintaining a constant pump speed is the current clinical standard and was achieved using a 10700 RPM set point and a PI controller ($K_P$=0.0028, $\tau$=5). The constant speed controller is referred to as the constant RPM controller. For the differential pressure controller, $\Delta P_d$ was estimated using the method described in Giridharan & Skliar, 2006. Briefly, $\Delta P_d$ was estimated using the measured pump speed, the estimated pump flow $F_P$, a Golay-Savitzky (GS) filter and an extended Kalman filter (EKF). $\Delta P_d$ reference set point was set to 87 mmHg. The differential pressure controller had a gain, $K_P$=0.003, time constant, $\tau$=5, and used a low-pass Butterworth filter with a 5-Hz cutoff frequency. The differential pressure controller is referenced as, ΔP control.

Comparison with Sensor-Based Control Algorithms.

The ΔRPM control algorithm disclosed herein was compared to the following sensor-based LVAD control algorithms proposed in literature: (1) a control based on left ventricular end diastolic pressure (LVEDP; see Bullister et al., 2002); and (2) a control based on mean aortic pressure (MAOP; see Wu et al., 2001). Mean aortic pressure control was achieved by setting the reference MAOP to 100 mmHg at which the pump flow was 5 l/min at rest. The gain, $K_P$ was set to 0.04, and time constant, $\tau$=5. The left ventricular end diastolic pressure control used a constant reference LVEDP of 7 mmHg at which the pump provided approximately 5 l/min at rest and used $K_P$=0.05, $\tau$=5. Efficacy and robustness of all algorithms was tested in-silico using (1) rest and exercise conditions, (2) a rapid eight-fold increase in pulmonary vascular resistance (PVR) under rest and exercise, (3) transitions from rest to exercise and exercise to rest, (4) safe mode during left heart fibrillation, and (5) 1% to 10% RPM measurement noise through (1) to (4). (4) and (5) were only applied to the disclosed ΔRPM control.

Safe Mode.

A safe mode was incorporated to switch to a constant RPM control when the mean pump speed drops below a certain threshold (8000 RPM) for longer than 10 seconds. The safe mode is advantageous in the event of an asystolic heart, as the differential pump speed will approach zero, and the controller will reduce pump speed to zero to prevent suction which can lead to hypoperfusion induced mortality and pump thrombosis. The safe mode maintains the mean pump speed at 8500 RPM to prevent pump stoppage and thrombosis in extreme conditions.

Example 1

Perfusion and Suction Prevention A: The Exemplary Controller (ΔRPM Control)

Figure 8:
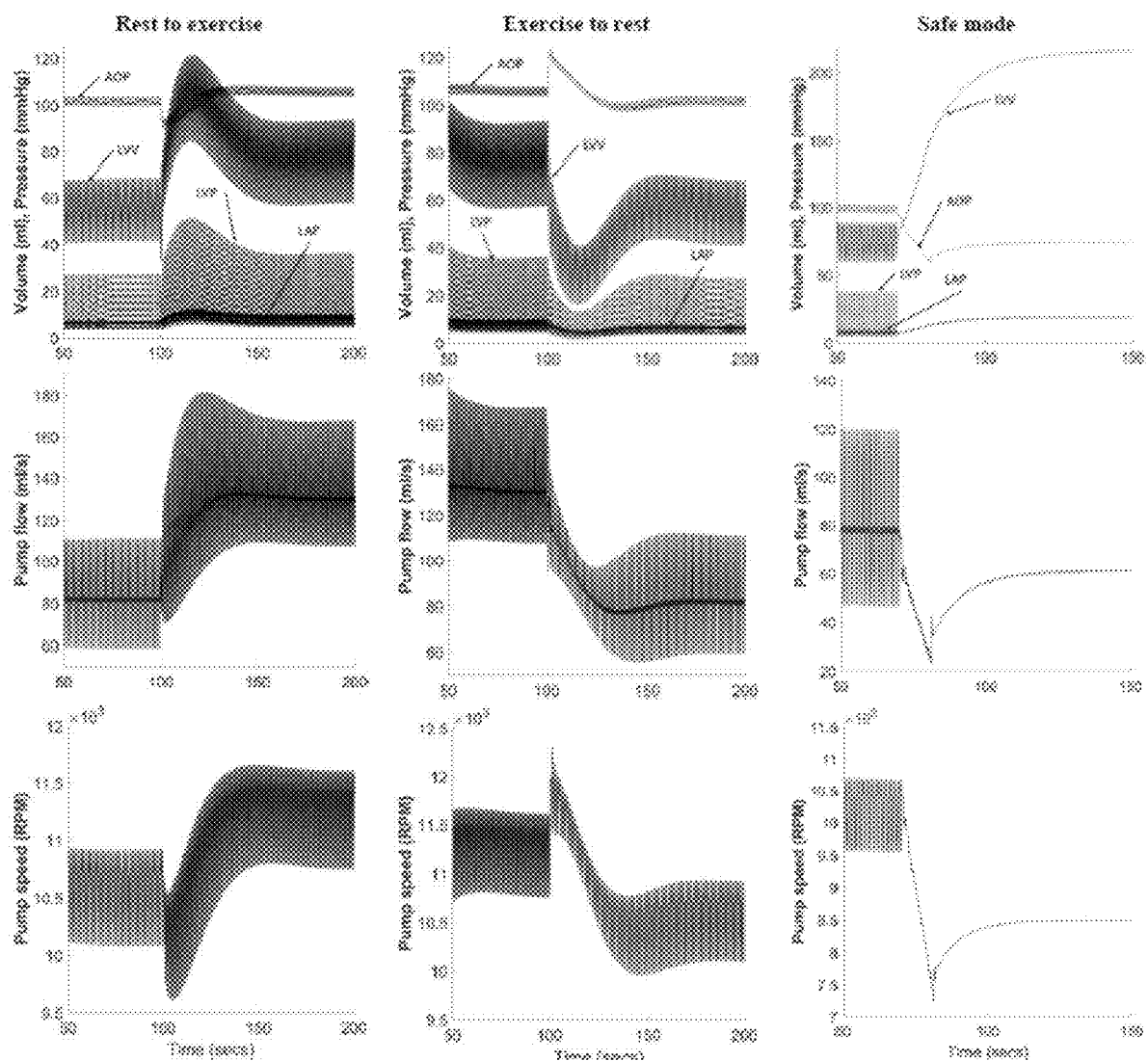
FIG. 8 is a series of graphs showing hemodynamic results using the presently disclosed controller (ΔRPM controller) during transition from rest to exercise and exercise to rest at t=100 seconds, and during asystole (t=70 seconds). The safe mode is triggered when the pump speed drops below 8000 RPM for longer than 10 s. A constant speed control then maintains the pump speed at 8500 RPM which reverts the heart to heart failure baseline.
Figure 9:
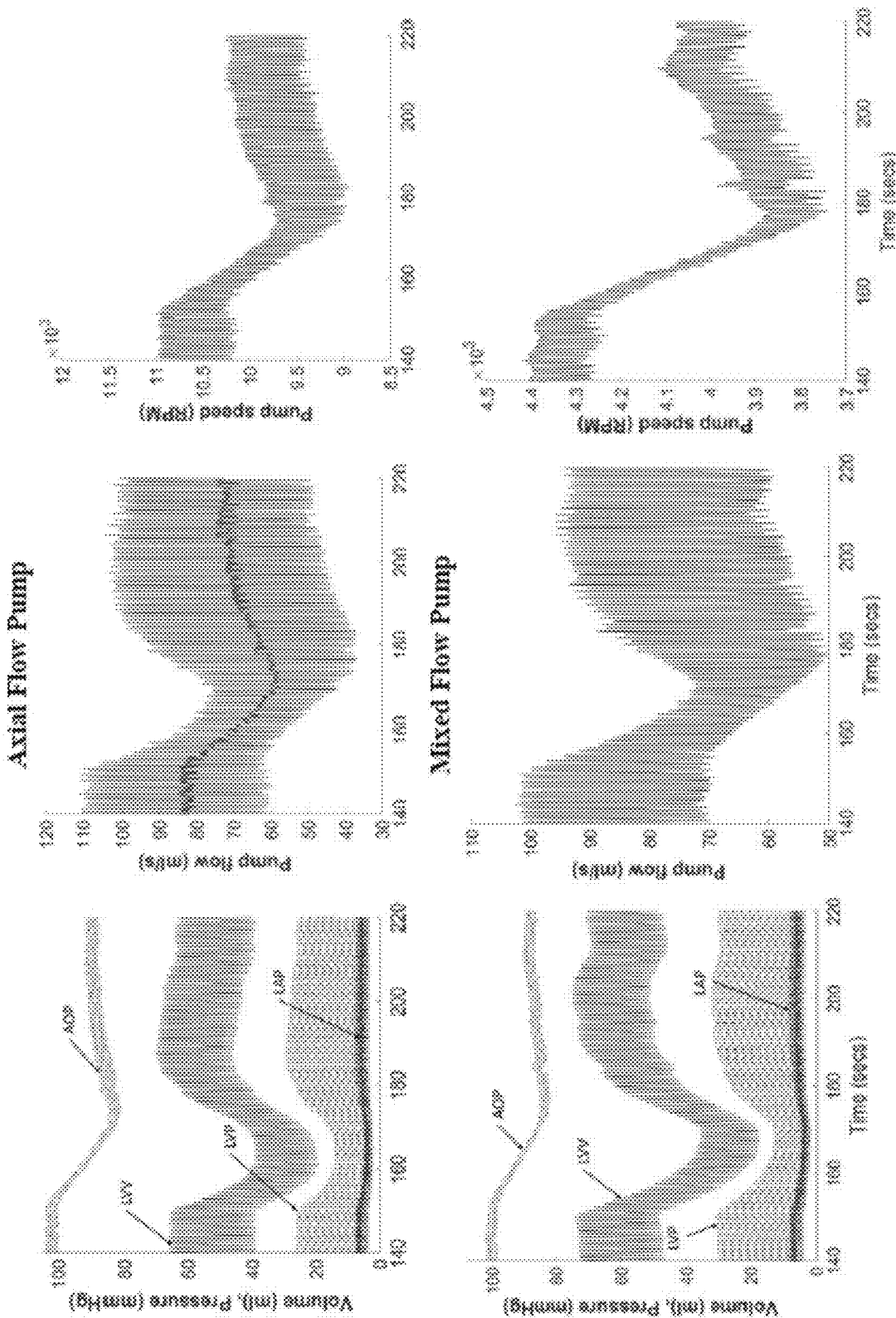
FIG. 9 is a series of graphs showing suction prevention during reduced preload (8× PVR) with an axial flow pump and a mixed flow pump. Increased PVR was initiated at t=150 seconds. The controller successfully prevented suction for both pumps with 1% normally distributed noise.

ΔRPM control algorithm successfully maintained physiologic perfusion and prevented ventricular suction in all test conditions and provided the greatest margin of safety to suction. The ΔRPM control algorithm increased LVAD flow from 5 l/min during rest to 8.0 l/min during exercise. As shown in Table 1 and FIG. 7, the controller prevented ventricular suction during a rapid eight-fold increase in pulmonary vascular resistance (PVR), limiting the ventricular end diastolic pressure drop to 5.6 mmHg at rest and 7.4 mmHg at exercise. The controller was also able to adapt to instantaneous transitions from rest to exercise and from exercise to rest (see FIG. 8). 95% of the steady state values for all tested cases were reached in less than 60 seconds. The ΔRPM control algorithm achieved similar results with the DP2 pump during rest and exercise and prevented ventricular suction with 8× PVR (FIG. 9).

TABLE 1

Control Outcomes During Multiple Test Conditions Using an Exemplary Controller as Compared to Four Different Controllers from the Literature

| | LTO (l/min) | AoP (mmHg) | LVEDP (mmHg) | LVV (ml) | Min LVP (mm Hg) | Suction? |
|---|---|---|---|---|---|---|
| REST | | | | | | |
| NH baseline | 5.0 | 122/78 | 8 | 85/147 | 5 | No |
| FH baseline | 3.7 | 96/63 | 16 | 181/229 | 9.5 | No |
| ΔRPM ctrl | 5.0 | 104/100 | 5.6 | 40/65 | 3.5 | No |
| CS ctrl | 5.0 | 104/100 | 5.4 | 36/63 | 3.3 | No |
| ΔP ctrl | 4.9 | 103/98 | 6.6 | 49/77 | 4.4 | No |
| EDP ctrl | 5.0 | 102/97 | 7 | 53/82 | 4.8 | No |
| MAOP ctrl | 5.0 | 103/98 | 6.3 | 46/74 | 4.1 | No |
| EXERCISE | | | | | | |
| NH baseline | 8.2 | 129/84 | 6.4 | 45/112 | 3.0 | No |
| FH baseline | 6.1 | 102/65 | 21 | 190/242 | 16.4 | No |

TABLE 1-continued

Control Outcomes During Multiple Test Conditions
Using an Exemplary Controller as
Compared to Four Different Controllers from the Literature

| | LTO (l/min) | AoP (mmHg) | LVEDP (mmHg) | LVV (ml) | Min LVP (mm Hg) | Suction? |
|---|---|---|---|---|---|---|
| ΔRPM ctrl | 8.0 | 108/104 | 7.4 | 58/94 | 5.2 | No |
| CS ctrl | 7.6 | 103/98 | 10 | 88/12 | 7.8 | No |
| ΔP ctrl | 7.9 | 106/102 | 8.2 | 68/104 | 6.0 | No |
| EDP ctrl | 8.1 | 108/105 | 7.0 | 54/89 | 4.9 | No |
| MAOP ctrl | 7.6 | 104/98 | 10.2 | 89/126 | 7.8 | No |
| | | | REST 8X PVR | | | |
| ΔRPM ctrl | 5.0 | 104/100 | 5.6 | 40/65 | 3.51 (3.1) | No |
| CS ctrl | 4.7 | 95/94 | 0.9 (−0.2) | 2/11 | 0.37 (−0.7) | YES |
| ΔP ctrl | 4.6 | 93/91 | 2.8 (0.8) | 14/34 | 1.5 (0.4) | YES (IS) |
| EDP ctrl | 4.3 | 90/85 | 7 (4.4) | 55/82 | 4.8 (3.7) | No |
| MAOP ctrl | —* | 100/99.9 | −3.7 (−3.7) | —* | −4.4 (−4.4) | YES |
| | | | EXERCISE 8X PVR | | | |
| ΔRPM ctrl | 7.0 | 96/92 | 7.2 (4.6) | 58/91 | 5.2 (3.1) | No |
| CS ctrl | 7.14 | 96/93 | 6.2 (5.0) | 49/80 | 4.5 (3.5) | No |
| ΔP ctrl | 7.3 | 98/95 | 4.8 (3.0) | 32/63 | 3.3 (1.8) | No |
| EDP ctrl | 7.1 | 96/92 | 7 (5.1) | 56/89 | 5.0 (3.5) | No |
| MAOP ctrl | 7.6 | 101/100 | 2.0 (2.8) | 9.3/32 | 1.4 (1.9) | YES |

LTO: left total output, AoP: Aortic pressure, LVEDP: Left ventricular end diastolic pressure, LVV: Left ventricular volume. LVP: Left ventricular pressure, IS: Intermittent suction. Values in parenthesis are the minimum transitional values during 8× PVR. ΔRPM ctrl: speed pulsatility control, ΔP ctrl: differential pressure control CS ctrl: constant speed control, EDP ctrl: end diastolic pressure control, MAOP ctrl: mean aortic pressure control.
*Note that during high levels of ventricular suction as in the MAOP control with reduced preload, the pump flow rate and ventricular volumes are variable and thus are not included in the table.

Example 2

Perfusion and Suction Prevention B: Constant RPM Control (Clinical Standard)

Figure 7A:
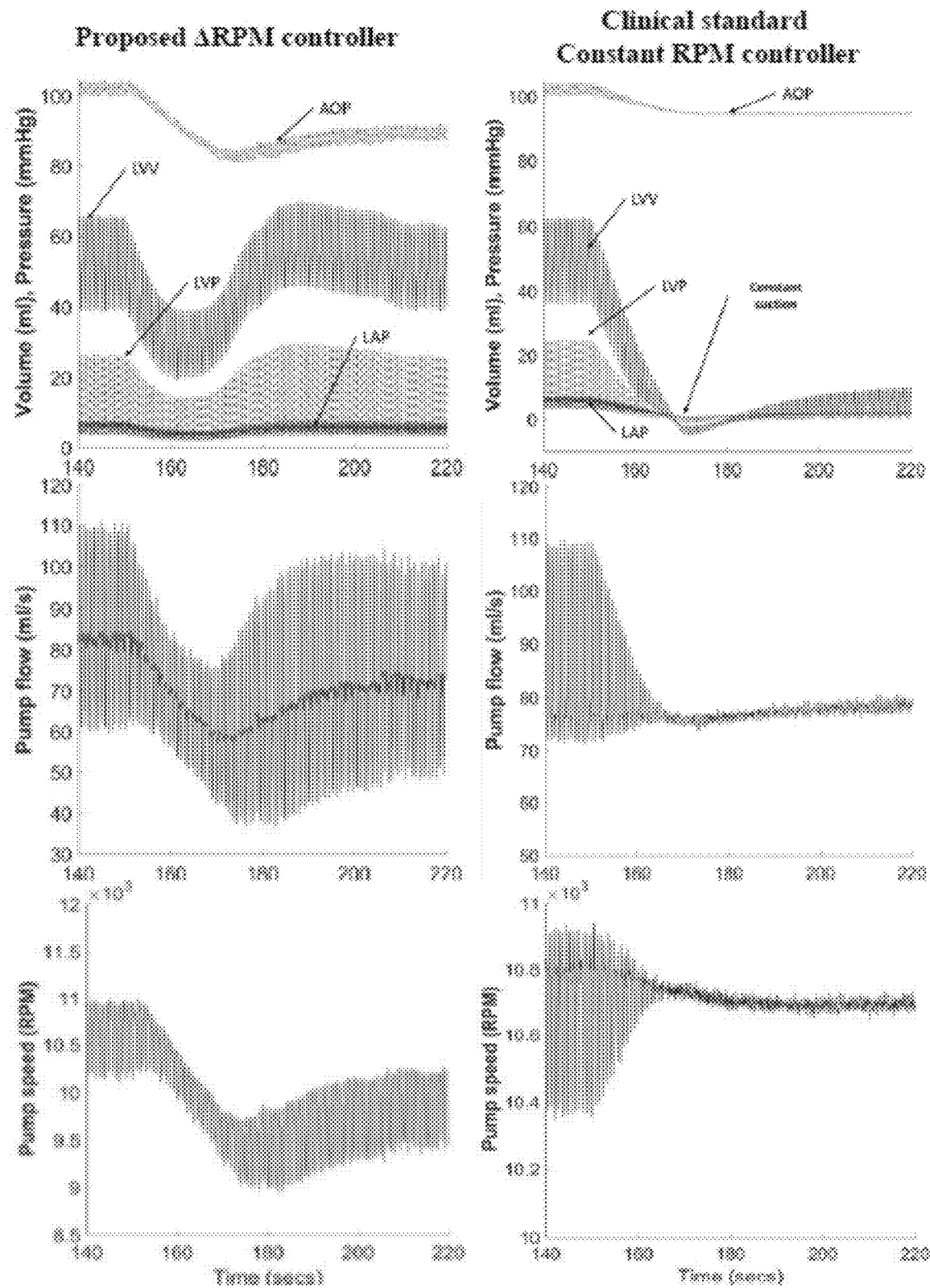
FIGS. 7A and 7B present a controller response comparison during rapid reduction in preload (8× PVR). The preload reduction was introduced at t=150 s for the ΔRPM, constant RPM, ΔP, and MAOP controllers. Constant suction is evident in constant speed control with end diastolic pressures below 1 mmhg at steady state. ΔP control caused intermittent suction during transition, but soon recovered afterwards. MAOP control, cause excessive constant suction. The proposed ΔRPM controller maintained the highest safety margin at steady state and during transition as seen with ventricular volume and pressure waveforms. AoP: Aortic pressure, LVP: Left ventricular end diastolic pressure, LVV: Left ventricular volume, LAP: Left atrial pressure, MAOP: Mean Aortic Pressure.
Figure 7B:
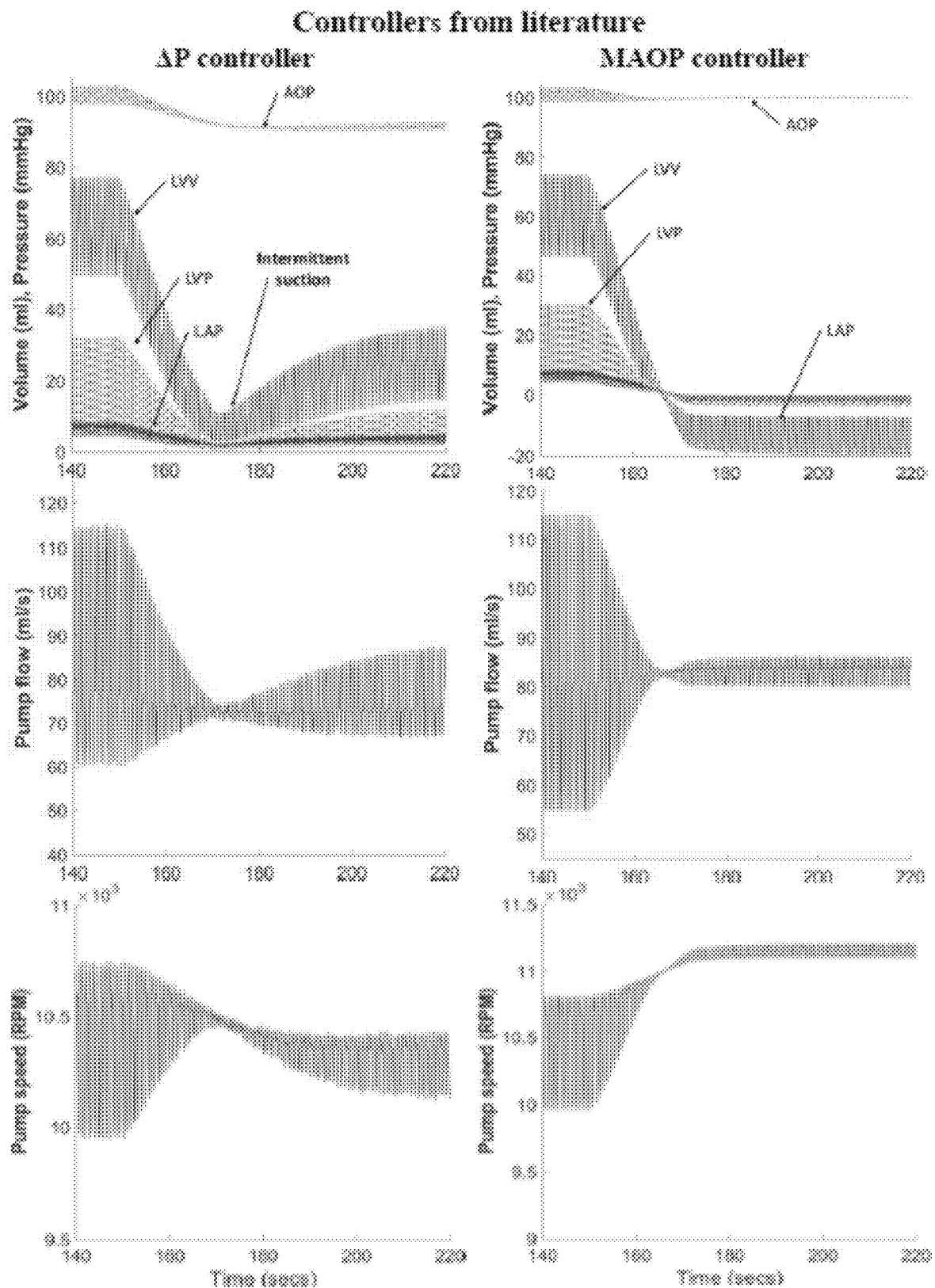

Maintaining a constant pump speed provided adequate perfusion during rest (5.0 l/min) without suction events (5.4 mmHg LVEDP). During exercise, the constant RPM control augmented flows but the overall pump flow rate was less than ΔRPM control. Significantly, during the rapid increase in PVR, constant RPM control caused suction at rest (steady state LVEDP=0.9 mmHg, with a LVEDP as low as −0.2 mmHg during transition; FIGS. 7A and 7B). Suction did not occur during exercise with an eight-fold increase in PVR with a minimum ventricular pressure of 3.1 mmHg. Transitions from rest to exercise and exercise to rest also did not trigger ventricular suction.

Example 3

Perfusion and Suction Prevention C: ΔP Control (Model-Based Estimation)

ΔP control maintained adequate perfusion during rest (4.93 l/min) and exercise (7.9 l/min). However, intermittent suction (IS) occurred during eight-fold PVR increase at rest (0.8 mmHg LVEDP during transition; FIGS. 7A and 7B), and soon recovered to 2.5 mmHg at steady state. The controller adapted well to instant transitions from exercise to rest and rest to exercise without any suction events.

Example 4

Perfusion and Suction Prevention D: MAOP Control (Sensor-Based Control)

Maintaining a reference mean aortic pressure (100 mmHg) led to adequate perfusion during rest (5.0 l/min), but lower flow rate during exercise (7.6 l/min). The MAOP control failed to adapt during reduced preload condition (8× PVR) with the onset of constant suction and negative LVEDP as shown in Table 1.

Example 5

Perfusion and Suction Prevention D: EDP Control (Sensor-Based Preload Control)

Preload control using direct measurement of ventricular pressure led to adequate perfusion during rest (5 l/min) and exercise (8.1 l/min) as well as protection against suction during reduced preload (FIG. 10) and instantaneous transition from exercise to rest and rest to exercise. This is expected since a control based on preload is effectively mimicking the natural Frank-Starling mechanism. However, with the introduction of sensor drift as low as 5 mmHg (with zero measurement noise) which is below the reported drift for similar inlet/outlet sensors (Shi et al., 2008; Brancato et al., 2016), EDP control performance deteriorated and intermittent suction was seen with 8× PVR during rest. Higher levels of sensor drift caused constant suction.

Example 6

Noise Tolerance

ΔRPM control was able to maintain physiologic perfusion and suction prevention with eight-fold PVR at rest with up to 6% noise while only using a moving average filter, as shown in Table 2. The controller caused intermittent suction with 7%, 8% and the control quality deteriorated completely with 10% noise. Any noise level greater than 6% caused some degree of suction or intermittent suction.

TABLE 2

Noise Tolerance of the Disclosed ARPM Control Algorithm with 1%, 4%, 6% Normally Distributed Noise

| | Actual ΔRPM | Filtered ΔRPM | LVEDP (mmHg) | LTO (l/min) | Suction? |
|---|---|---|---|---|---|
| | | | 1% | | |
| Rest | 798 | 793 | 5.6 | 5.0 | No |
| Exercise | 818 | 766 | 7.4 | 8.0 | No |
| Rest 8× PVR | 817 | 764 | 7.1 (4.6) | 4.4 | No |
| | | | 4% | | |
| Rest | 667 | 711 | 4.8 | 5.0 | No |
| Exercise | 622 | 684 | 6.3 | 8.1 | No |
| Rest 8× PVR | 596 | 665 | 3 (1.5) | 4.3 | No |
| | | | 6% | | |
| Rest | 398 | 745 | 3.2 | 5.3 | No |
| Exercise | 455 | 667 | 4.8 | 8.2 | No |
| Rest 8× PVR | 513 | 723 | 2.8 (−0.2) | 4.5 | YES (IS) |

Values in parenthesis are the minimum transitional values during 8× PVR. After 6% noise, control deteriorated, and intermittent or constant suction events occurred.

Example 7

Safe Mode

The safe mode first detected the onset of asystole when the pump speed dropped below 8000 RPM for longer than 10 seconds. The controller automatically switched to a constant speed control and maintained the pump flow rate at 3.7 l/min which is equivalent to the cardiac output of the unassisted failing heart (see Table 1) and caused no suction at rest. FIG. 8 demonstrates the safe mode with left heart asystole induced at t=70 s and the controller response to maintain the mean pump speed at 8500 RPM at rest.

Discussion of EXAMPLES 1-7

EXAMPLES 1-7 show the use of the proposed control algorithm under different physiologic conditions with two objectives: (1) physiologic perfusion; and (2) suction prevention. In silico results demonstrated the feasibility of the proposed ΔRPM control algorithm to adapt pump flow to physiologic demand and prevent ventricular suction over a wide range of conditions. The novelty of proposed algorithm is the choice of the control variable (ΔRPM), which, even with a simple PI controller, is able to achieve physiologic control and suction prevention with only a single constant ΔRPM setpoint. Importantly, the ΔRPM control achieved adequate perfusion during rest and exercise and prevented suction even during rapid transitions from rest to exercise and from exercise to rest and during a rapid reduction in preload (eight-fold increase in PVR), which happens physiologically with the Valsalva maneuver, or during coughing but to a lower extent. The performance of the proposed control algorithm was demonstrated to be superior to the current clinical standard using constant speed control where ΔRPM control provided higher or equivalent flow and protection against suction. Additionally, we implemented the proposed algorithm using a mixed flow pump (DP2) and were able to achieve similar results and adequate perfusion suction prevention, illustrating pump independence of the algorithm (FIG. 9).

The presently disclosed control algorithm synchronized the ventricular assist provided by the LVAD to the natural control mechanisms of the body. As an example, increased venous return during exercise will lead to a higher preload and an increase in ventricular contractility due to Frank-Starling mechanism. The increase in ventricular contractility leads to an increased ΔRPM, which will cause the controller to increase the pump speed and flow to maintain the desired ΔRPM setpoint. Similarly, a decrease in perfusion demand would lead to a reduction in contractility, resulting in the controller reducing the pump speed and flow and thereby preventing over pumping and suction. Hence, the control algorithm utilizes the body's own sympathetic and parasympathetic control mechanism to achieve sensorless control of the pump to match the perfusion demand and avoid suction.

Figure 10:
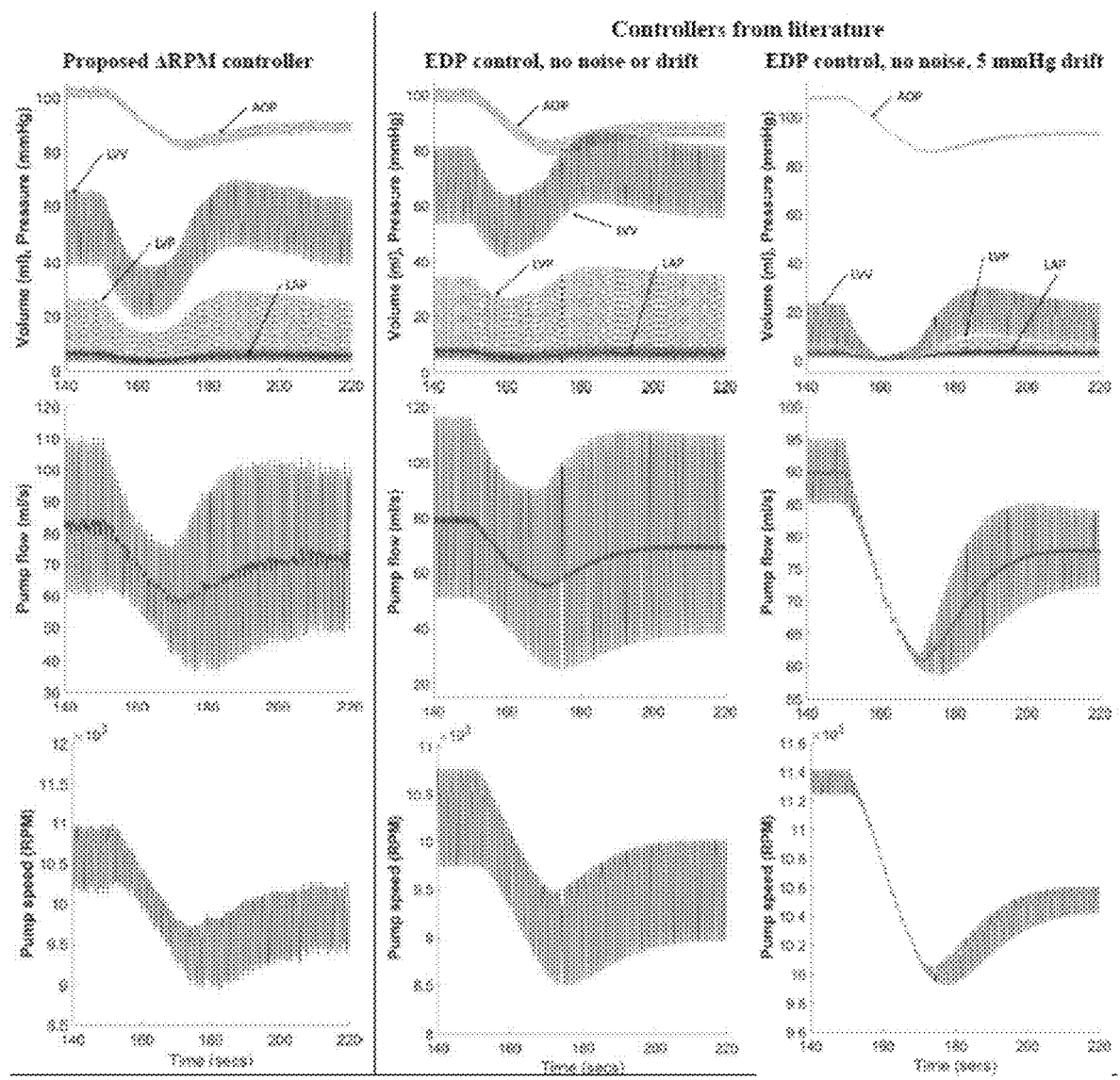
FIG. 10 is a series of graphs showing control comparisons using EDP control with and without a 5 mmHg inlet pressure sensor drift during 8× PVR. Intermittent suction was seen transitionally as the left ventricular volume and pressure fell rapidly but soon recovered. Current implantable pressure sensor technologies have reported >4× higher sensor drifts in 1 year. It is important to note that for EDP control was used with a single EDP reference point.

Control based on preload has been proposed in literature (see e.g., Ochsner et al., 2014; Mansouri et al., 2015). In these approaches, a direct measurement of preload (end diastolic pressure (Mansouri et al., 2015), end diastolic volume (Ochsner et al., 2014)), a combination of ventricular pressure with afterload impedance estimations (Moscato et al., 2010), or heartrate and aortic pressure (Bullister et al. 2002), have been used to adjust the pump flow and speed. In these controllers, the use of a single reference point can sufficiently prevent ventricular suction and provide adequate perfusion (AlOmari et al., 2013). However, it requires pressure or ventricular volume sensors for direct measurement, which suffer from low long-term reliability and drift (Shi et al., 2008; Brancato et al., 2016). Thus, these sensors have not been tested chronically in vivo. The results presented herein demonstrated that even with a 5 mmHg drift was introduced to the measurement, EDP control caused intermittent suction (FIG. 10).

Wu et al., 2001 attempted to achieve physiologic control based solely on afterload through the measurement of aortic pressure. While the strategy of maintaining a reference mean aortic pressure provided sufficient perfusion at rest and exercise, it failed to prevent suction as it does not take ventricular filling into account and causes suction (Table 1, FIG. 2). Several control schemes have modified such control to account for both preload and after load (e.g. Wu et al., 2003; Moscato et al., 2010).

Salamonsen et al., 2012 showed that the relation between pump speed and pump speed pulsatility is fairly linear when the aortic valve is closed. However, this linearity is lost during partial support. In their work, they opted for the use of flow pulsatility as a measurement of preload over pump speed pulsatility because flow pulsatility maintained a more linear relationship during partial support. However, pump speed pulsatility is readily available while pump flow must be estimated. Further, estimation of pump flow using parametric and model based methods are reported to have low robustness and accuracy and are susceptible to blood viscosity changes (Pauls et al., 2016). The selection of the appropriate ΔRPM setpoint is critical to the proposed controller performance. A high ΔRPM setpoint can lead to lower perfusion while a low ΔRPM setpoint can increase the potential for ventricular suction. However, in the simulations presented herein, it has been shown that the appropriate selection of a single ΔRPM setpoint can simultaneously satisfy both objectives of physiologic control and suction prevention. The control algorithm only required measurement of pump speed, which is an intrinsic pump parameter, obviating the need for implantation of unreliable pressure or flow sensors. In addition, it did not require frequent adjustment of setpoints (e.g., pump speed). A priori pump model estimation was also not required, which eliminated modeling errors and model estimation errors induced by patient's blood viscosity changes or circadian variations. It should be noted that the presently disclosed algorithm did not detect suction per se, but rather detected the approach towards suction and reduced the pump speed to prevent such events. Furthermore, the presently disclosed algorithm did not require pump design modifications and can be readily incorporated into existing blood pumps.

Rotor speed measurements can be obtained through phase currents or hall effect sensors, which typically have <1% normally distributed noise. The controller maintained physiologic perfusion and prevented suction for up to 6% noise, demonstrating its robustness (Table 2). The simplicity of the control structure is a direct result of the control objective which is based on pump speed pulsatility. Controlling the differential pump speed sets no boundaries on the mean pump speed, which allows for adequate pump flow and perfusion during rest and exercise or during vascular changes as long as suction is prevented. Hence, the controller can tolerate the temporal variabilities associated with the cardiovascular system (e.g. circadian variation) and intrapatient variabilities. While pump speed pulsatility was used herein, other intrinsic pump parameters that are sensitive to pressure head changes across the pump (e.g., changes in pump current) may also be used for physiologic control and suction prevention.

The presently disclosed controller required the LVAD to be sensitive to pressure head changes and some degree of reserve ventricular contractile function to cause changes in pump speed during a cardiac cycle. The native cardiac contractility which is present even in patients with end-stage heart failure (~15-20% ejection fraction), is adequate to cause changes in pump speeds for the proposed algorithm to work, as demonstrated herein. The presently disclosed controller, however, could fail during ventricular asystole/fibrillation when the ventricular contractility becomes negligible resulting in a low ΔRPM. The low ΔRPM would lead to the controller reducing the pump speed and flow below physiologic levels. To mitigate this, a safe mode was implemented to maintain a constant pump speed in the event of left heart asystole to maintain pump flows at basal levels (heart failure baseline) and potentially sustain life while avoiding pump thrombosis and suction (FIG. 8). When the heart is in asystole/fibrillation, the lack of ventricular contraction results in a low delta RPM to which the controller responds by reducing the RPM. However, the delta RPM value will not increase as there is no effective contraction of the myocardium even if the RPM value is at the lowest clinically recommended RPM of the pump. Thus, the safe mode operates at a clinically recommended minimum RPM, to minimize risk of pump thrombosis and ensures ~3.7 L/min of flow, equivalent to heart failure baseline to help sustain life. This sensing is achieved by monitoring the pump mean speed and switching to a constant speed reference point when the mean pump speed falls below the threshold for longer than 10 seconds.

It should be noted that ventricular fibrillation and asystole can lead to patient mortality if not reversed quickly, even if the LVAD was pumping, due to the lack of flow to the lungs. The safe mode ensures that the lack of pump flow does not cause mortality and keeps the pump viable by preventing thrombosis in the event of a resuscitation of the patient. The performance of the proposed controller may diminish in the event of pump thrombosis and inflow/outflow cannula kinking which affects the dynamics of the LVAD and change the measured ΔRPM. These extenuating clinical conditions may require a change in the ΔRPM setpoint by a clinician for physiologic control and suction prevention.

The lumped parameter circulatory system model employed herein was based at least in part on certain assumptions. Firstly, it assumes blood as a Newtonian fluid, the heart valves as ideal valves (i.e. no regurgitation, no pressure drop and instant closure), and did not incorporate gravitational effects. The model cannot replicate all expected clinical responses, including baroreceptor or neurohumoral responses. However, this previously validated circulatory system model demonstrated the feasibility of the ΔRPM control algorithm for physiologic perfusion and suction prevention. Mock flow loop and large animal studies are needed to validate the controller performance and demonstrate its long-term safety, efficacy and reliability.

Thus, the presently disclosed subject matter provides in some embodiments a sensorless control algorithm for continuous flow ventricular assist device that provides physiologic perfusion and prevent ventricular suction. The presently disclosed algorithm requires only the measurement of intrinsic pump speed, eliminating the need for implantable sensors or model-based estimation methods. The in-silico results demonstrated feasibility and robustness of the proposed sensorless control algorithm over a wide range of clinical test conditions and measurement noise levels. The presently disclosed control algorithm does not require any pump design modifications and may be readily incorporated into existing blood pumps.

Example 8

Pulsatility Augmentation Using Sensor-Based Feedback Control with Normal PVR

In this EXAMPLE, the control objective of augmenting vascular pulsatility was added. Here, the controller used two reference differential pump speeds ΔRPM: a high reference $\Delta RPM_{Hr}$ and low reference $\Delta RPM_{Lr}$. The left ventricular and aortic pressure signals and flow rate through the CFL-VAD support with HF setting are given in FIGS. 3A-3D (left four panels). The aortic pressure changed between 77 and 120 mmHg, resulting in mean aortic pressure and pulse pressure as 98 and 43 mmHg, respectively, and the cardiac output was 4.9 L/min, similar to the results with the normal heart and superior to those with failing heart under rest condition (Table 1). In comparison, with the constant RPM control algorithm, the aortic pressure varied between 95 and 102 mmHg, while the mean aortic pressure was 98 mmHg and total output was 4.9 L/min, but the pulse pressure was only 7 mmHg and the value of actual ΔRPM was significantly diminished (FIGS. 3E-3H). During exercise, the pulse pressure with sensor-based method was lower than that with normal and failing heart but still obviously augmented compared to the constant RPM strategy. Furthermore, there was no suction phenomenon for all simulated conditions.

Example 9

Pulsatility Augmentation Using Sensorless Feedback Control with Normal PVR

The results with sensorless feedback control were similar to those with sensor-based method, such that the aortic pressure varied between 76 and 116 mmHg, the mean aortic pressure was 101 mmHg, and the pulse pressure was 40 mmHg under rest condition (FIGS. 3I-3L). In addition, the sensorless control algorithm enhanced LVAD flow rates from baseline HF values during rest and provided physiologic perfusion by increasing LVAD flow rates during exercise. The total flow rates were similar to the human circulatory system with a normal heart at rest and exercise conditions, respectively, and the pulse pressure generated with sensorless control algorithm outperformed that with constant RPM control algorithm (Table 3). No suction was observed during all test conditions.

TABLE 3

Pulsatility Augmentation: Comparisons of the Performances of a Sensor-based Control Algorithm, a Sensorless Control Algorithm, and a Constant RPM Control Strategy with an Axial CFLVAD Assistance Under Different Clinical and Physical Activity Conditions

|  | Total output (Lpm) | AoP (mmHg) | Pulse pressure (mmHg) | Mean AoP (mmHg) | Steady state actual mean ΔRPM | Steady state filtered mean ΔRPM |
|---|---|---|---|---|---|---|
| *Normal heart, No CFLVAD support* | | | | | | |
| Rest | 5.0 | 120/79 | 41 | 99 | N/A | N/A |
| Light exercise | 8.3 | 121/76 | 45 | 98 | N/A | N/A |
| *Failing heart, No CFLVAD support* | | | | | | |
| Rest | 3.8 | 97/63 | 34 | 79 | N/A | N/A |
| Light exercise | 6.5 | 97/60 | 37 | 77 | N/A | N/A |
| *Failing heart, Constant RPM control algorithm with normal PVR* | | | | | | |
| Rest | 4.9 | 102/95 | 7 | 98 | 566 | N/A |
| Light exercise | 8.0 | 98/92 | 6 | 95 | 589 | N/A |
| *Failing heart, Proposed control algorithm with normal PVR* | | | | | | |
| Rest[1] | 4.9 | 120/77 | 43 | 98 | 1184 | N/A |
| Rest[2] | 5.0 | 116/76 | 40 | 101 | 1160 | 1075 |
| Light exercise[1] | 8.1 | 107/82 | 25 | 95 | 1198 | N/A |
| Light exercise[2] | 8.0 | 104/83 | 21 | 94 | 1226 | 1123 |
| *Failing heart, Constant RPM control algorithm with rapidly increased PVR* | | | | | | |
| Rest | 4.7 | 97/92 | 5 | 94 | 376 | N/A |
| Light exercise | 7.7 | 93/89 | 4 | 91 | 429 | N/A |
| *Failing heart, Proposed control algorithm with rapidly increased PVR* | | | | | | |
| Rest[1,H] | 4.6 | 116/70 | 46 | 92 | 1239 | N/A |
| Rest[2,H] | 4.6 | 109/66 | 43 | 93 | 1166 | 1078 |
| Rest[1,L] | 4.6 | 117/71 | 46 | 93 | 1242 | N/A |
| Rest[2,L] | 4.6 | 109/66 | 43 | 93 | 1166 | 1078 |
| Light exercise[1,H] | 7.6 | 103/77 | 26 | 89 | 1283 | N/A |
| Light exercise[2,H] | 7.5 | 99/73 | 26 | 89 | 1227 | 1081 |
| Light exercise[1,L] | 7.5 | 103/78 | 25 | 89 | 1281 | N/A |
| Light exercise[2,L] | 7.5 | 99/73 | 26 | 89 | 1228 | 1081 |

[1] sensor-based algorithm,
[2] sensorless algorithm,
[H] PVR increased when $\Delta RPM_{Hr}$ held,
[L] PVR increased when $\Delta RPM_{Lr}$ held,
AoP: aortic pressure. Suction status was negative for all entries.

These results demonstrated that the proposed algorithm generated adequate vascular pulsatility while providing sufficient physiologic perfusion and avoiding suction for all simulated conditions.

Example 10

Pulsatility Augmentation Using Sensor-Based and Sensorless Feedback Control with Increased PVR With rapidly increased 5-fold PVR (initiated time was varied when $\Delta RPM_{Hr}$ or $\Delta RPM_{Lr}$ held), there was no obvious performance degradation between the sensor-based (FIGS. 4A-4D) and sensorless (FIGS. 4I-4L) control algorithms. However, compared to the results with normal PVR, a transient reduction in the hemodynamic and LVAD parameters were observed with the axial CFLVAD with the onset of rapid reduction in PVR, aortic pressure, mean aortic pressure, and total outputs were slightly decreased, but pulse pressure was almost unchanged at rest and exercise conditions (Table 1). The same trend was found with the constant RPM control strategy except that the pulse pressures were only no larger than 5 mmHg at rest and exercise conditions. In addition, suction was not observed with all the control algorithms even during an abrupt, non-physiologic, step-transition from exercise to rest condition (FIG. 5).

Discussion of EXAMPLES 8-10

EXAMPLES 8-10 show the use of the presently disclosed control algorithm with three control objectives: (1) physiologic perfusion; (2) suction prevention; and (3) pulsatility augmentation. The results demonstrated that the arterial pulsatility for CFLVADs can be enhanced significantly by modulating and controlling ΔRPM, and CFLVADs operating at constant pump speeds significantly reduced vascular pulsatility. In addition, based on the proposed algorithm, arterial, ventricular hemodynamic, and LVAD parameters waveforms were altered compared to the constant RPM method by switching two thresholds as $\Delta RPM_{Lr}$ and $\Delta RPM_{Hr}$. However, the mean aortic pressure and pump flow rates were guaranteed without obviously being decreased. Therefore, the proposed control strategy may have potential advantages over the constant RPM algorithm, especially considering achieving a desired myocardial oxygen supply or left ventricular unloading, even providing theoretical basis and technology support for developing some related weaning protocols for the patients, whose myocardial functions could be possibly recovered without negatively affecting the average mean aortic pressure and pump flow rates (Ising et al., 2011).

It has been also reported that diminished vascular pulsatility due to CFLVAD assistance especially under constant RPM mode negatively influenced aortic vessels, aortic wall, and smooth muscle cells (Segura et al., 2013; Ambardekar et al., 2015; Ross et al., 2018). This phenomenon was also related to some adverse events including aortic insufficiency, arteriovenous malformations, hemorrhagic strokes, and gastrointestinal bleeding (Soucy et al., 2013a; Cheng et al., 2014). The increase in vascular pulsatility with the proposed control algorithm may prevent or help reduce the severity of the above adverse events associated with diminished vascular pulsatility.

The sensorless control algorithm performance disclosed herein was comparable to the closed-loop performance of the sensor-based algorithm that required direct measurement of pump speed differential ($\Delta$RPM) for all tested conditions, without obvious performance degradation (Table 1). Except for increasing vascular pulsatility and providing adequate physiologic perfusion, LV suction was prevented even under extreme conditions of five-fold rapid changes in PVR (e.g. Valsalva or coughing) or excessive physical activity. The low/high reference differential pump speeds, $\Delta$RPM$_{Lr}$/$\Delta$RPM$_{Hr}$, were set at 800/1400 RPM with sensorless algorithm compared to 750/1650 RPM with the sensor-based algorithm. The higher $\Delta$RPM$_{Lr}$ setpoint and lower $\Delta$RPM$_{Hr}$ setpoint for the sensorless algorithm were required due to integration of RPM measurement noise (1% uniformly distributed noise) and measurement of pump speeds at 100 Hz, which were comparable to the commercially available pump speed sensors, and integrated into our model to reflect potential real-world conditions (Meki et al. 2019).

The augmented vascular pulsatility with the proposed sensor-based and sensorless algorithms were not at the same frequency as the native heartbeat (asynchronous flow modulation control strategy). The advantage of using asynchronous control is that it does not require a triggering source (sensorless control; Soucy et al., 2015), and achieved physiologic vascular pulsatility compared to other modulation modes such as synchronous copulse and counterpulse (Ising et al., 2011). In literature, asynchronous flow modulation algorithm for CFLVADs have shown that the high LVAD flow generated suction events which would require suction detection and prevention algorithms to be embedded into the system. It also limited the minimum flow rate to 1 L/min to prevent retrograde flow (backflow; Ising et al., 2011). The above steps may increase complexity of the open-loop system. However, in the proposed asynchronous feedback control algorithm for $\Delta$RPM modulation avoided suction events for all tested conditions, even under the worst-case (non-physiologic) test conditions, defined by a rapid (<20 sec) five-fold increase in PVR.

Disclosed herein are exemplary feedback control systems that provide advantages by controlling $\Delta$RPM modulation in order to increase vascular pulsatility in computer simulation. It is true that the in-silico model cannot take the place of in-vitro or in-vivo models, and cannot replicate all clinical observations expected (Ising et al., 2011). Moreover, the lumped parameter model in this study assumed Newtonian blood, instantaneously open and closed heart valves, constant compliance for all non-active blocks. The proposed control algorithm cannot enable aortic valve opening, and the actual modulated beating frequency was too low under exercise condition. Despite these limitations, the computer simulation model demonstrated the feasibility of the proposed control algorithm for increasing vascular pulsatility and maintaining adequate physiologic perfusion, while at the same time avoiding ventricular suction, which needs further validation in mock loop and large animal models.

Thus, disclosed herein are new control algorithms for CFLVADs that were developed to enhance vascular pulsatility, provide sufficient cardiac output, and avoid ventricular suction. The algorithms were implemented with the CFLVAD intrinsic pump speed, used to obtain modulation of pump speed differentials. The computer simulation findings demonstrated feasibility and robustness of the proposed sensor-based and sensorless control algorithms, and predict acceptable function and efficacy over the wide range of expected clinical test conditions.

REFERENCES

All references listed below, as well as all references cited in the instant disclosure, including but not limited to all patents, patent applications and publications thereof, scientific journal articles, and database entries, are incorporated herein by reference in their entireties to the extent that they supplement, explain, provide a background for, or teach methodology, techniques, and/or compositions employed herein. The discussion of the references is intended merely to summarize the assertions made by their authors. No admission is made that any reference (or a portion of any reference) is relevant prior art. Applicant reserves the right to challenge the accuracy and/or pertinence of any cited reference.

AlOmari et al. (2009) Non-invasive estimation of pulsatile flow and differential pressure in an implantable rotary blood pump for heart failure patients. Physiol Meas 30:371-86.

AlOmari et al. (2013) Developments in control systems for rotary left ventricular assist devices for heart failure patients: a review. Physiol Meas 34:R1-27.

Amacher et al. (2013) Control of ventricular unloading using an electrocardiogram-synchronized Thoratec paracorporeal ventricular assist device. J Thorac Cardiov Surg 146(3):710-717.

Ambardekar et al. (2015) Changes in aortic wall structure, composition, and stiffness with continuous-flow left ventricular assist devices: a pilot study. Circ Heart Fail 8:944-952.

Ambardekar et al. (2018) Coronary Artery Remodeling and Fibrosis With Continuous-Flow Left Ventricular Assist Device Support. Circ Heart Fail 11(5):e004491.

Amit et al. (2017) Dynamic change in aortic vascular stiffness in patients bridged to transplant with continuous-flow left ventricular assist devices. JACC: Heart Failure 5:449-459.

Ayre et al. (2000) Sensorless Flow and Head Estimation in the VentrAssist Rotary BloodPump. Artificial Organs 24:585-588.

Ayre et al. (2003) Non-invasive flow estimation in an implantable rotary blood pump: a study considering non-pulsatile and pulsatile flows. Physiol Meas 24:179-89.

Benjamin et al. (2017) Heart Disease and Stroke Statistics—2017 Update: A Report From the American Heart Association. Circulation 135:e146-e603.

Bozkurt et al. (2014) Arterial pulsatility improvement in a feedback-controlled continuous flow left ventricular assist device: an ex-vivo experimental study. Med Eng Phys 36(10):1288-1295.

Brancato et al. (2016) An Implantable Intravascular Pressure Sensor for a Ventricular Assist Device. Micromachines 7:135.

Bullister et al. (2002) Physiologic Control Algorithms for Rotary Blood Pumps Using Pressure Sensor Input. Artificial Organs 26:931-938.

Cheng et al. (2014) Comparison of continuous-flow and pulsatile-flow left ventricular assist devices: is there an advantage to pulsatility? Annals of Cardiothoracic Surgery 3:573-581.

Choi et al. (1997) Modeling and identification of an axial flow blood pump. Proceedings of the 1997 American Control Conference (Cat. No. 97CH36041), pages 3714-3715.

Choi et al. (2007) Hemodynamic controller for left ventricular assist device based on pulsatility ratio. Artif Organs 31(2):114-125.

Couperus et al. (2017) Pump Speed Optimization in Stable Patients with a Left Ventricular Assist Device. ASAIO Journal 63:266-272.

Cox et al. (2009) A mathematical model to evaluate control strategies for mechanical circulatory support. Artif Organs 33(8):593-603.

Farrar et al. (2007) Design Features, Developmental Status, and Experimental Results With the Heartmate III Centrifugal Left Ventricular Assist System With a Magnetically Levitated Rotor. ASAIO Journal 53:310-315.

Frazier (2010) Unforeseen consequences of therapy with continuous-flow pumps. Circ Heart Fail 3:647-649.

Frazier et al. (2010) Optimization of axial-pump pressure sensitivity for a continuous-flow total artificial heart. J Heart Lung Transplant 29:687-91.

Fukamachi et al. (2010) An innovative, sensorless, pulsatile, continuous-flow total artificial heart: device design and initial in vitro study. J Heart Lung Transplant 29(1):13-20.

Fukamachi et al. (2013) Preload Sensitivity in Cardiac Assist Devices. The Annals of Thoracic Surgery 95:373-380.

Gao et al. (2012) A pulsatile control algorithm for continuous-flow pump for heart recovery. ASAIO J 58(4):343-352.

Garcia et al. (2008) Effects of pulsatile- and continuous-flow left ventricular assist devices on left ventricular unloading. J Heart Lung Transpl 27:261-267.

Giridharan & Skliar (2006) Physiological Control of Blood Pumps Using Intrinsic Pump Parameters: A Computer Simulation Study. Artificial Organs 30:301-307.

Giridharan et al. (2002) Modeling and control of a brushless DC axial flow ventricular assist device. ASAIO J 48:272-89.

Giridharan et al. (2006) Predicted hemodynamic benefits of couterpulsation therapy using a superficial surgical approach. ASAIO J 52(1):39-46.

Griffith et al. (2001) HeartMate II left ventricular assist system: from concept to first clinical use. Ann Thorac Surg 71(3):S116-S120.

Guan et al. (2010) Physiologic benefits of pulsatile perfusion during mechanical circulatory support for the treatment of acute and chronic heart failure in adults. Artif Organs 34:529-536.

Hasin et al. (2015) Attenuation in peripheral endothelial function after continuous flow left ventricular assist device therapy is associated with cardiovascular adverse events. Circulation Journal 79:770-777.

Huang et al. (2014) Pulse-pressure-enhancing controller for better physiologic perfusion of rotary blood pumps based on speed modulation. ASAIO J 60(3):269-279.

Ising et al. (2011) Flow modulation algorithms for continuous flow left ventricular assist devices to increase vascular pulsatility: a computer simulation study. Cardiovasc Eng Technol 2(2):90-100.

Ising et al. (2015) Feasibility of pump speed modulation for restoring vascular pulsatility with rotary blood pumps. ASAIO J 61(5):526-532.

Jahren et al. (2014) Analysis of pressure head-flow loops of pulsatile rotodynamic blood pumps. Artif Organs 38(4): 316-326.

Karantonis et al. (2007) Noninvasive Pulsatile Flow Estimation for an Implantable Rotary Blood Pump. in 2007 29th Annual International Conference of the IEEE Engineering in Medicine and Biology Society 1018-1021.

Khalil et al. (2008) Preload sensitivity of the Jarvik 2000 and HeartMate II left ventricular assist devices. ASAIO Journal 54:245-248.

Kirklin et al. (2017) Eighth annual INTERMACS report: Special focus on framing the impact of adverse events. The Journal of Heart and Lung Transplantation 36:1080-1086.

Konishi et al. (1994) Dynamic systemic vascular resistance in a sheep supported with a Nimbus AxiPump. ASAIO J 40:M299-M302.

Lim et al. (2008) Noninvasive average flow and differential pressure estimation for an implantable rotary blood pump using dimensional analysis. IEEE Trans Biomed Eng 55:2094-101.

Malagutti et al. (2007) Noninvasive average flow estimation for an implantable rotary blood pump: a new algorithm incorporating the role of blood viscosity. Artif Organs 31:45-52.

Mansouri et al. (2015) Preload-based starling-like control for rotary blood pumps: numerical comparison with pulsatility control and constant speed operation. PLoS One 10:e0121413.

Meki et al. (2019) A sensorless rotational speed-based control system for continuous flow left ventricular assist devices. IEEE Trans Biomed Eng. DOI: 10.1109/TBME.2019.2928826.

Michael et al. (2014) Starling-Like Flow Control of a Left Ventricular Assist Device: In Vitro Validation. Artificial Organs 38:E46-E56.

Moscato et al. (2010) Left Ventricle Afterload Impedance Control by an Axial Flow Ventricular Assist Device: A Potential Tool for Ventricular Recovery. Artificial Organs 34:736-744.

Ochsner et al. (2014) A physiological controller for turbodynamic ventricular assist devices based on a measurement of the left ventricular volume. Artif Organs. 38:527-38.

Patibandla et al. (2016) Evaluation of the effect of diminished pulsatility as seen in continuous flow ventricular assist devices on arterial endothelial cell phenotype and function. J Heart Lung Transplant 35:930-932.

Pauls et al. (2016) Evaluation of Physiological Control Systems for Rotary Left Ventricular Assist Devices: An In-Vitro Study. Ann Biomed Eng 44:2377-2387.

Pennings et al. (2013) Pump flow estimation from pressure head and power uptake for the HeartAssist5, HeartMate II, and HeartWare VADs. ASAIO J 59:420-6.

Petrou et al. (2018a) Comparison of Flow Estimators for Rotary Blood Pumps: An In Vitro and In Vivo Study. Annals of Biomedical Engineering 46:2123-2134.

Petrou et al. (2018b) Viscosity Prediction in a Physiologically Controlled Ventricular Assist Device. IEEE Transactions on Biomedical Engineering 65:2355-2364.

Pillay & Krishnan (1989) Modeling, simulation, and analysis of permanent-magnet motor drives. II. The brushless DC motor drive. IEEE Transactions on Industry Applications 25:274-279.

Rose et al. (2001) Long-term use of a left ventricular assist device for end-stage heart failure. N Engl J Med 345:1435-1443.

Ross et al. (2018) Left ventricular assist devices and the kidney. Clin J Am Soc Nephrol 13:348-355.

Salamonsen et al. (2012) Theoretical Foundations of a Starling-Like Controller for Rotary Blood Pumps. Artificial Organs. 36:787-796.

Saxton & Andrews (1960) An ideal heart pump with hydrodynamic characteristics analogous to the mammalian heart. Trans Am Soc Artif Intern Organs 6:288-91.

Segura et al. (2013) Morphologic changes in the aortic wall media after support with a continuous-flow left ventricular assist device. J Heart Lung Transplant 32:1096-1100.

Sen et al. (2016) Mechanical circulatory assist devices: a primer for critical care and emergency physicians. Critical Care (London, England) 20:153-153.

Shi et al. (2008) Development of an Auto Calibration Method for the Implantable Blood Pressure Sensor in the Undulation pump ventricular assist device (UPVAD). 7th Asian-Pacific Conference on Medical and Biological Engineering, Berlin, Heidelberg, 66-69.

Simaan et al. (2009) A dynamical state space representation and performance analysis of a feedback-controlled rotary left ventricular assist device. IEEE Trans Control Syst Technol 17(1):15-28.

Slaughter et al. (2009a) Advanced heart failure treated with continuous-flow left ventricular assist devices. N Engl J Med 361:2241-2251.

Slaughter et al. (2009b) Intraoperative evaluation of the HeartMate II flow estimator. J Heart Lung Transplant 28:39-43.

Soucy et al. (2013a) Defining pulsatility during continuous-flow ventricular assist device support. J Heart Lung Transplant 32:581-587.

Soucy et al. (2013b) Fault detection in rotary blood pumps using motor speed response. ASAIO J 59(4):410-419.

Soucy et al. (2015) Rotary pump speed modulation for generating pulsatile flow and phasic left ventricular volume unloading in a bovine model of chronic ischemic heart failure. J Heart Lung Transplant 34(1):122-131.

Soucy et al. (2017) Continuous-flow left ventricular assist device support improves myocardial supply: demand in chronic heart failure. Ann Biomed Eng 45:1475-1486.

Stanfield et al. (2013) In vitro pulsatility analysis of axial-flow and centrifugal-flow left ventricular assist devices. J Biomech Eng 135:034505-1-034505-6.

Stevens et al. (2011) Frank-starling control of a left ventricular assist device. 2011 Annual International Conference of the IEEE Engineering in Medicine and Biology Society 1335-1338.

Ündar (2005) Benefits of pulsatile flow during and after cardiopulmonary bypass procedures. Artif Organs 29:688-690.

Uriel et al. (2012) Development of a Novel Echocardiography Ramp Test for Speed Optimization and Diagnosis of Device Thrombosis in Continuous-Flow Left Ventricular Assist Devices: The Columbia Ramp Study. Journal of the American College of Cardiology 60:1764-1775.

Uriel et al. (2013) Long Term Outcomes for LVAD Patients Who Underwent Speed Optimization Using Pre-Discharge Ramp Test, The Journal of Heart and Lung Transplantation. 32:S182.

Vandenberghe et al. (2005) Hemodynamic modes of ventricular assist with a rotary blood pump: continuous, pulsatile, and failure. ASAIO J 51(6):711-718.

Voigt et al. (2005) Suction detection for the MicroMed DeBakey Left Ventricular Assist Device. ASAIO J 51:321-8.

Vollkron et al. (2004) Development of a suction detection system for axial blood pumps. Artif Organs 28:709-16.

Wang & Simaan (2013) A Suction Detection System for Rotary Blood Pumps Based on the Lagrangian Support Vector Machine Algorithm, IEEE Journal of Biomedical and Health Informatics 17:654-663.

Wang et al. (2015) Rotary blood pump control strategy for preventing left ventricular suction. ASAIO J 61:21-30.

Wang et al. (2018a) Sensor-Based Physiologic Control Strategy for Biventricular Support with Rotary Blood Pumps. ASAIO J 64:338-350.

Wang et al. (2018b) Sensorless Physiologic Control, Suction Prevention, and Flow Balancing Algorithm for Rotary Biventricular Assist Devices. IEEE Transactions on Control Systems Technology 27:1-13.

Wu et al. (2001) Physiological Control of a Ventricle Assist Device. Annals of Biomedical Engineering 29:S-2.

Wu et al. (2003) An Advanced Physiological Controller Design for a Left Ventricular Assist Device to Prevent Left Ventricular Collapse. Artificial Organs 27:926-930.

It will be understood that various details of the presently disclosed subject matter can be changed without departing from the scope of the presently disclosed subject matter. Furthermore, the foregoing description is for the purpose of illustration only, and not for the purpose of limitation.

What is claimed is:

1. A method for controlling a ventricular assist device, the method comprising:
   receiving at least one reference pump speed differential associated with a pump of a ventricular assist device;
   determining a filtered or non-filtered pump speed differential associated with the pump of a ventricular assist device, wherein the filtered pump speed differential is based on multiple measurements using a phase current sensor or a hall effect sensor; and
   adjusting, using a feedback based controller algorithm, current or power to the pump based on the at least one reference pump speed differential and the filtered pump speed differential.

2. The method of claim 1, wherein the feedback based controller algorithm includes a proportional controller algorithm, a proportional-integral controller algorithm, a proportional-integral-derivative controller algorithm, a proportional-derivative controller algorithm, a fuzzy logic algorithm, an optimal control algorithm, or other control algorithm.

3. The method of claim 1, wherein determining a filtered pump speed differential includes determining an average rotational pump speed differential over a period of time.

4. The method of claim 1, wherein determining the filtered pump speed differential and adjusting the current to the pump is performed without using a pressure sensor, without using a priori pump model estimation, and/or without using a flow sensor.

5. The method of claim 1, wherein the pump is an axial flow pump powered by a brushless direct current motor or any other type of motor.

6. The method of claim 1, wherein adjusting, using the feedback based controller algorithm, current or power to the pump based on the at least one reference pump speed differential and the filtered pump speed differential includes alternating between a first reference pump speed differential and a second reference pump speed differential of the at least one reference pump speed as input to the feedback based controller algorithm so as to induce pulsatility, wherein the second reference pump speed differential is different than the first reference pump speed differential.

7. The method of claim 1, comprising:
    detecting that the average filtered pump speed differential or average filtered pump speed meets or is below at least one safe mode activation threshold value; and
    in response to detecting the average filtered pump speed differential or average filtered pump speed meets or is below the at least one safe mode activation threshold value, triggering a safe mode for the pump, whereby the pump is set to maintain a constant pump speed.

8. The method of claim 7, wherein the safe mode is triggered during ventricular fibrillation, left ventricular asystole, arrhythmia, or other adverse cardiac event.

9. The method of claim 7, wherein the at least one safe mode activation threshold value includes a predetermined average filtered pump speed differential or average filtered pump speed value being detected for longer than a user-defined period of time.

10. A system for controlling a ventricular assist device, the system comprising:
    a non-transitory computer readable medium; and
    a controller implemented using the non-transitory computer readable medium, wherein the controller is configured for:
        receiving at least one reference pump speed differential associated with a pump of a ventricular assist device;
        determining a filtered pump speed differential associated with the pump of a ventricular assist device, wherein the filtered pump speed differential is based on multiple measurements using a phase current sensor or a hall effect sensor; and
        adjusting, using a feedback based controller algorithm, current to the pump based on the at least one reference pump speed differential and the filtered pump speed differential.

11. The system of claim 10, wherein the feedback based controller algorithm includes a proportional controller algorithm, a proportional-integral controller algorithm, a proportional-integral-derivative controller algorithm, a proportional-derivative controller algorithm, a fuzzy logic algorithm, an optimal control algorithm, or other control algorithm.

12. The system of claim 10, wherein determining a filtered pump speed differential includes determining an average rotational pump speed differential over a period of time.

13. The system of claim 10, wherein the controller is configured for determining the filtered pump speed differential and adjusting the current to the pump without using a pressure sensor, without using a priori pump model estimation, and/or without using a flow sensor.

14. The system of claim 10, wherein the controller is configured for:
    alternating between a first reference pump speed differential and a second reference pump speed differential of the at least one reference pump speed differential as input to the feedback based controller algorithm so as to induce pulsatility, wherein the second reference pump speed differential is different than the first reference pump speed.

15. The system of claim 10, wherein the controller is further configured for:
    detecting that the average filtered pump speed differential or average filtered pump speed meets or is below at least one safe mode activation threshold value; and
    in response to detecting the average filtered pump speed differential or average filtered pump speed meets or is below the at least one safe mode activation threshold value, triggering a safe mode for the pump, whereby the pump is set to maintain a constant pump speed.

16. The system of claim 15, wherein the safe mode is triggered during ventricular fibrillation, left ventricular asystole, arrhythmia, or other adverse cardiac event.

* * * * *